(12) United States Patent
Kost et al.

(10) Patent No.: US 8,589,180 B2
(45) Date of Patent: *Nov. 19, 2013

(54) THIRD PARTY ORDERING FROM A DRUG SAMPLE FULFILLMENT SYSTEM

(75) Inventors: Cecil Kost, Chapel Hill, NC (US); Timothy Chrobuck, Seattle, WA (US); Scott M. King, Issaquah, WA (US); David V. Tovrea, Lake Stevens, WA (US); Susan T. Burrows, Bothell, WA (US); Steven E. Singer, Woodinville, WA (US); Zachary K. Hector, Woodinville, WA (US)

(73) Assignee: Skyscape.com, Inc., Marlborough, MA (US)

( * ) Notice: Subject to any disclaimer, the term of this patent is extended or adjusted under 35 U.S.C. 154(b) by 52 days.

This patent is subject to a terminal disclaimer.

(21) Appl. No.: 13/294,517

(22) Filed: Nov. 11, 2011

(65) Prior Publication Data

US 2012/0059666 A1 Mar. 8, 2012

Related U.S. Application Data

(63) Continuation of application No. 10/674,904, filed on Sep. 30, 2003, now Pat. No. 8,082,173.

(60) Provisional application No. 60/472,956, filed on May 22, 2003.

(51) Int. Cl.
    *G06Q 10/00* (2012.01)
(52) U.S. Cl.
    USPC .................................. 705/2; 705/3

(58) Field of Classification Search
    USPC ............................................. 705/2
    See application file for complete search history.

(56) References Cited

U.S. PATENT DOCUMENTS

| | | | |
|---|---|---|---|
| 4,971,362 A | 11/1990 | Lapsker | |
| 5,628,530 A | 5/1997 | Thornton | |
| 6,564,121 B1 | 5/2003 | Wallace | |
| 6,629,135 B1 | 9/2003 | Ross | |
| 2002/0032582 A1* | 3/2002 | Feeney et al. | 705/2 |
| 2002/0065683 A1 | 5/2002 | Pham | |
| 2003/0120550 A1* | 6/2003 | Peyrelevade et al. | 705/26 |

OTHER PUBLICATIONS

Brown, J., "For Consumers Free Samples Are a Virtual Reality: Pharmaceutical Samples Were Once Strictly Passed From Manufacturer to Physician to Patient, but Online Marketing Tactics Are Rearranging That Order," Med Ad News 21(1):36-37, Jan. 2002.
Brown, J., "Samples of the Future (Estimated Retail Worth of Drug Samples Dispensed in 2000 Was $7.95 Bil or Some 50% of the Promotional Spending: New Technology to Improve Monitoring)," Med Ad News 20(7):3, Jul. 2001.

(Continued)

*Primary Examiner* — Hiep V Nguyen
(74) *Attorney, Agent, or Firm* — John H. Pearson, Jr., Esq.; Walter F. Dawson, Esq.; Pearson & Pearson, LLP

(57) ABSTRACT

A process to facilitate the fulfillment of drug samples to prescribers in several different manners. A sales representative can request actual drug samples on-line or can order on-line coupons for drug samples to be shipped to a prescriber and from which the prescriber distributes to his patient.

20 Claims, 16 Drawing Sheets

(56) References Cited

OTHER PUBLICATIONS

"iPhysicianNet and MedManage Systems Partner to Offer a New Electronic and Voucher Sampling Service to Thousands of U.S. Physicians," PR Newswire, Apr. 24, 2001.

"MedManage Systems Enhances Online Drug Sample Voucher System for Physicians," PR Newswire, Jul. 16, 2001.

"MedManage Systems, Inc. Names Cecil Kost President and CEO," PR Newswire, Apr. 4, 2002.

"MedManage™ Leads Shift in Drug Sampling Practices Online Vouchers," PR Newswire, Sep. 17, 2001.

"RxCentric and MedManage Systems Partner to Expand Physician Use of Innovative Online Drug Sampling—Alliance Gives Pharmaceutical Companies Broader Physician Access to Drug Detailing and Sampling Programs," Business Wire, Mar. 20, 2001.

SamplesMD (Secure e-Sampling), "SamplesMD™: A Partner for Growth With the Pharmaceutical Industry," Business Plan, © Jan. 2000, 29 pages.

SamplesMD (Secure e-Sampling), Presentation Slides, Apr. 13, 2001, 19 pages.

SamplesMD (Secure e-Sampling), "SamplesMD Application" (online), Jul. 11, 2001, 14 pages.

SamplesMD (Secure e-Sampling), "A Partner for Growth With the Pharmaceutical Industry," Presentation Slides, Jan. 2002, 25 pages.

Silverman, J., "Vouchers Replace Rx Samples in Bid to Stop Abuse," Clinical Psychiatry News 29(7):60, Jul. 2001.

Tice, C., "MedManage Tracks Troublesome Pill Samples," Puget Sound Business Journal 21(2):7, May 19, 2000.

\* cited by examiner

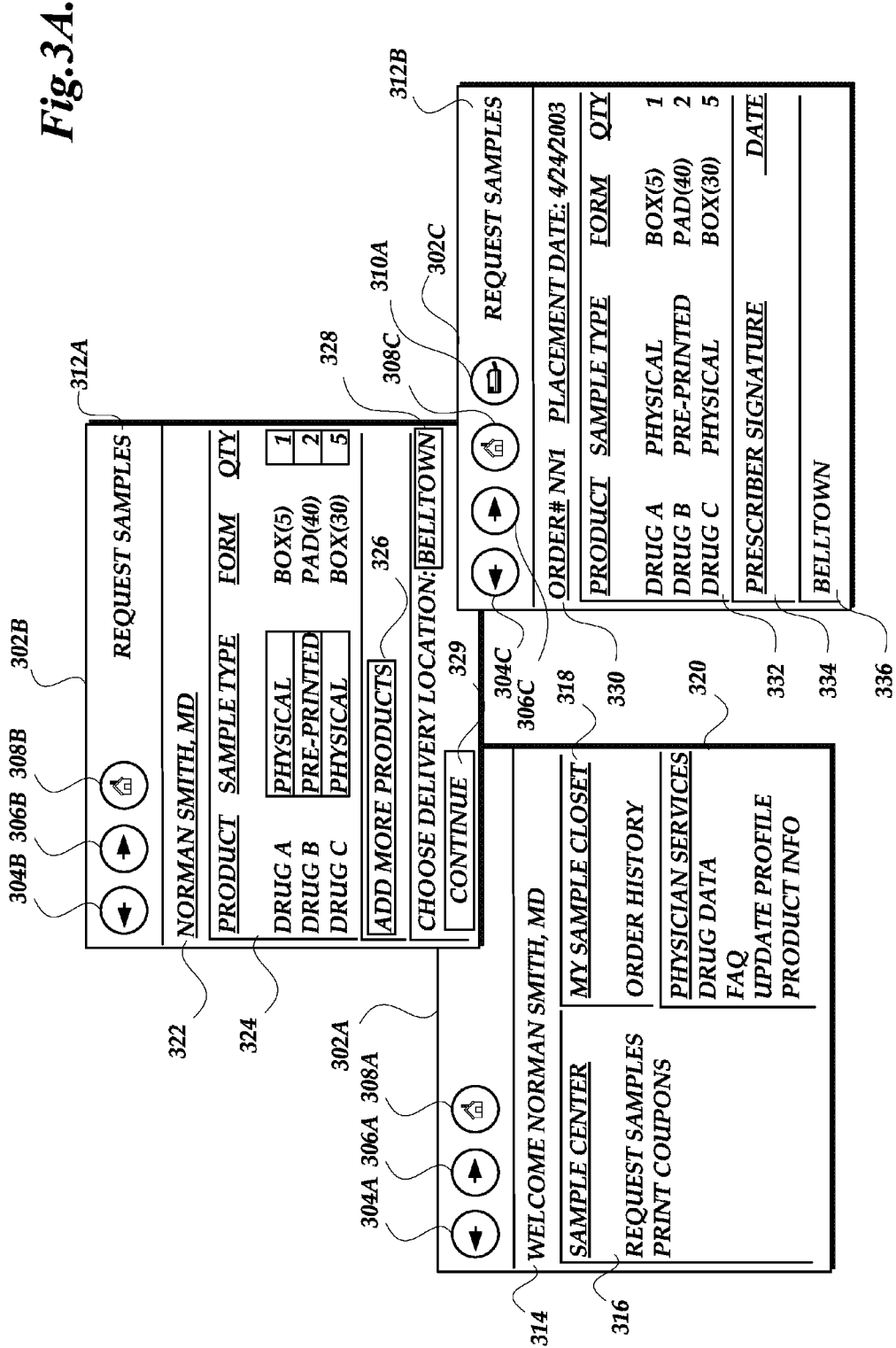

*Fig.3B.*

PRINT SAMPLES — 342
CANCEL
NORMAN SMITH, MD      DRUG A — 344
PATIENT NAME — 346
DATE    CONTROL #23    GROUP ID 9 — 348
        DRUG A - GENERIC LABEL — 350
6 SIGNATURE  (VALID UNTIL 5/24/00) — 352
PRESCRIBER SIGNATURE      DEA 27 — 354

302E, 308E, 310B, 304E, 306E

NORMAN SMITH, MD
I HAVE READ AND AGREE TO TERMS...
PRODUCT:       DRUG A
DISCLAIMER:    TAKE WITH FOOD
PRINT NUMBER:  3
LOCATION:      BELLTOWN
WHO:           AGENT OF PHYSICIAN
NAME:          LISA SMITH, MANAGER
               CONTINUE — 341

302D, 304D, 306D, 308D, 338, 340

THIRD PARTY ORDERING FROM A DRUG SAMPLE FULFILLMENT SYSTEM

CROSS-REFERENCE TO A RELATED APPLICATION

This application is a continuation of application Ser. No. 10/674,904, filed Sep. 30, 2003, which claims the benefit of Provisional Application No. 60/472,956, filed May 22, 2003, both of which are incorporated herein by reference.

FIELD OF THE INVENTION

The present invention relates generally to an architecture for distributing drug samples, and more particularly, to the design of software relating to drug sample fulfillment incorporating protocols and means for expansion and interfacing with other systems.

BACKGROUND OF THE INVENTION

From idea to production, the development of a new drug can take up to 10 years and cost about $800 million. But many risks abound in the development process that can cause complete failure. The process usually starts with the idea that an existing chemical substance has therapeutic value or that the structure of an existing drug can be modified for new clinical uses. Out of 10,000 chemicals tested in a laboratory, only one may eventually become a drug. Besides the expense necessary to produce them, drugs are heavily regulated by the bureaucracy of government agencies. In the United States, the FDA not only approves new drugs, but also determines how drugs are produced and sold by continually monitoring the development and use of all drugs sold. This is the backdrop against which a pharmaceutical company ("pharma 102") markets its precious few developed drugs 104. See FIG. 1.

Traditionally, a sales representative 106 of the pharma 102 visits one or more prescribers 110, leaves behind some drug samples of the drugs 104, and waits in trust that the prescribers 110 will prescribe these drug samples to their patients. When a sales representative 106 visits a prescriber, such as one of the prescribers 110, the sales representative 106 is performing two actions together called a drug detail. First, the sales representative 106 educates the prescriber about the efficacy of the drug samples for various disease states and differentiates them from any competitive drugs in the marketplace. Second, the sales representative 106 leaves drug samples behind with the prescriber so that he can dispense these drug samples to his patients. A triangle 108 hierarchically organizes all prescribers into deciles, which are numbers that divide a frequency distribution (the regularity of which a prescriber prescribes drugs) into 10 classes such that each contains the same number of prescribers. The upper 1-3 deciles describe one or more prescribers 110. The remaining 4-10 deciles describe one or more prescribers 112. Prescribers at deciles 1-3 comprise 25 percent of all prescribers and generate 50 percent of all prescriptions. The remaining 75 percent of prescribers are at deciles 4-10 and prescribe the remaining 50 percent of all other prescriptions. Because individual prescribers at deciles 4-10 do not generate as much income for the pharma 102 compared to those in the top three deciles, the sales representative 106 typically does not visit these prescribers, but instead, focuses her efforts on prescribers 110 at deciles 1-3.

The reason for this is mainly economic. For each sales representative 106, the pharma 102 incurs numerous expenses including purchasing and maintaining an automobile for the sales representative 106 to travel to the prescribers, and paying a salary, benefits, and so on. Also a growing number of billions of dollars are spent each year on everything necessary to support the distribution of drug samples, such as packaging and delivery. When this cost is multiplied by the cost of employing multiple sales representatives, the pharma 102 cannot afford to visit all prescribers to solicit patronage of its drugs.

But there are still other reasons beyond the economic ones that prevent the sales representative 106 from visiting all prescribers. One or more prescribers 112 may be located in remote areas making it difficult for the sales representative 106 to reach them. Certain prescribers 112 do not wish to see a sales representative 106 because they are too busy with their practice or they belong to an organization, such as a hospital, that forbids sales representatives from soliciting prescribers on its premises. Another reason why most prescribers 112 are not visited by the sales representative 106 has to do with absences by the sales representative 106 because of parental leaves, military duties, firings, layoffs, or unexpectedly resignations, and so on.

While it is cost prohibitive for the pharma 102 to send sales representatives to visit all prescribers, prescribers who know about the drug samples and want access to drug samples have problems too. If the prescriber were to be interested in designing a therapy from five different brands of drugs, he might have to track down five different sales representatives to get the drug samples. The prescriber's preferences are completely ignored. The biggest dissatisfaction of all among prescribers, however, is the lack or inconsistent supply of physical samples in their hands. These prescribers may not have easy access to the sales representative 106. And even if access were possible, the sales representative 106 may not have a ready supply of physical samples for these prescribers to use. The literature has shown that if a prescriber is dissatisfied with a drug brand due to lack of physical samples, the prescriber will not prescribe that particular drug brand to patients.

When the sales representative 106 leaves drug samples with the prescriber, the prescriber signs an acknowledgment indicating that these drug samples are now in his possession. Beyond that, however, there is no data that tracks whether drug samples actually get prescribed to patients of the prescriber. No additional information is possible beyond the point at which drug samples are given to the prescriber. So even though the pharma 102 has spent a great deal of money on drug samples, it has no means of knowing whether the physical samples were actually prescribed to patients or tossed uselessly into a garbage can. Without a way to track these drug samples, the pharma 102 cannot improve its drug sample distribution. Moreover, without tracking, expired drug samples may be prescribed to patients, diminishing their efficacy. This may add to wrongful impressions by patients regarding the drug's effectiveness and eventually will lead to a lack of acceptance of the drug in the marketplace.

In sum, not only is it expensive and laborious to develop new drugs, but the traditional drug sample distribution process does not allow the pharma 102 to assess the effectiveness of its drug sample fulfillment program further increasing financial risk to the pharma 102. Not all prescribers can be reached by the sales representative 106, hence limiting the distribution of drug samples to patients who may benefit from them. On the other hand, prescribers who do wish to have an opportunity to try the drug samples cannot obtain a consistent supply. Thus, there is a need for an architecture for enhancing drug sample fulfillment distribution while avoiding or reducing the foregoing and other problems.

SUMMARY

In accordance with an aspect of this subject matter, a method form of the subject matter includes a method for ordering drug samples, which comprises receiving access request via the Internet to a drug sample fulfillment platform from a brand Web site or another brand Web site. The method further comprises allowing a sales representative to order drug samples for a prescriber specified by a set of brand rules which include physical samples, vouchers, or coupons. The time frame, dosages and quantity of drug samples are different depending on whether the prescriber is a member of the one brand Web site or a member of another brand Web site.

In accordance with another aspect of this subject matter, a system form of the subject matter includes a system for ordering drug samples, which comprises a pharma rules sample engine configured to modify allocation of drug samples to a prescriber based on its monitoring of drug samples to the prescriber. The system further comprises hardware configured to run software for receiving access request via the Internet to a drug sample fulfillment platform from a brand Web site or another brand Web site; and allowing a sales representative to order drug samples for the prescriber specified by a set of brand rules which include physical samples, vouchers, or coupons. The time frame, dosages and quantity of drug samples are different depending on whether the prescriber is a member of the one brand Web site or a member of another brand Web site.

In accordance with a further aspect of this subject matter, a computer-readable medium form of the subject matter includes computer-readable medium on which stored computer-executable instructions to implement a method for ordering drug samples, which comprises receiving access request via the Internet to a drug sample fulfillment platform from a brand Web site or another brand Web site; and allowing a sales representative to order drug samples for a prescriber for drugs specified by a set of brand rules which time frame, dosages and quantity of drug samples being different depending on whether the prescriber is a member of the one brand Web site or a member of another brand Web site.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A is a pictorial diagram illustrating various Web pages associated with the drug sample fulfillment platform, according to one embodiment of the present invention;

FIG. 3B is a pictorial diagram illustrating various Web pages of a drug sample fulfillment distribution platform, according to one embodiment of the present invention.

DETAILED DESCRIPTION OF THE PREFERRED EMBODIMENT

Figure 1:
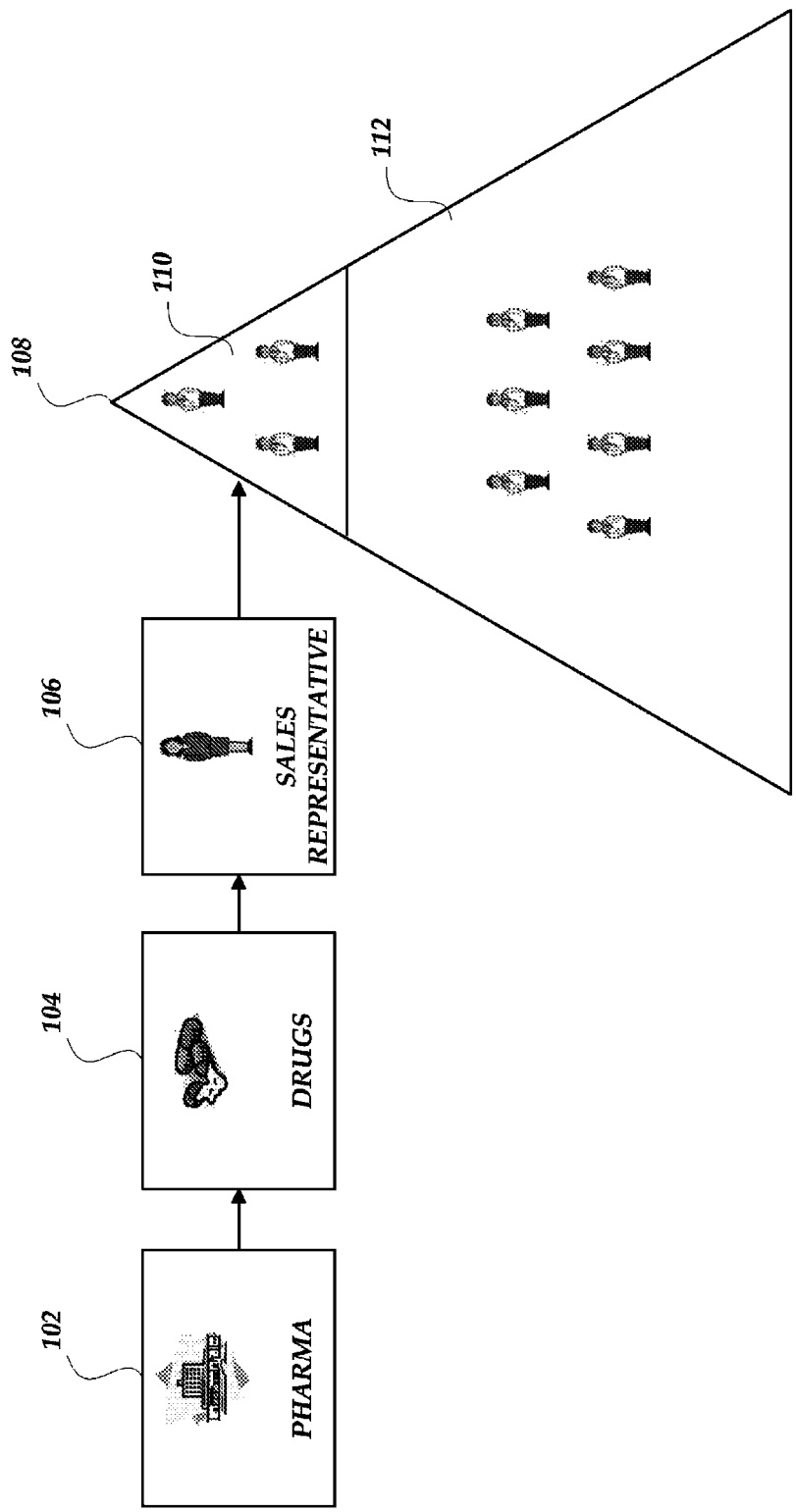
FIG. 1 is a block diagram illustrating a conventional system showing various problems of distributing drug samples to prescribers.

A system in which drug samples 212 are distributed to one or more prescribers 210 without the need to employ sales representatives is illustrated. A pharma 202 is a company engaged in the manufacture and sale of pharmaceuticals, which are medicinal drugs used for therapeutic applications. The term "prescribers" as referred to herein includes, but is not limited to, physicians; physician assistants; certified registered nurse practitioners; advanced registered nurse practitioners; and other licensed professionals authorized to prescribe medications.

Throughout a series of stages through which a drug passes during its lifetime, starting with its launch, continuing with its maturation in the marketplace, and concluding with the end of its patent life cycle, a brand manager 204 is assigned by the pharma 202 to manage the drug sample distribution to prescribers 210. The brand manager 204 begins a drug sample distribution program by first identifying a group of prescribers 210.

The brand manager 204 selects these prescribers 210 by excluding or including each prescriber based on criteria defined by the brand manager 204 (e.g., medical practice specialty, therapeutic class to which drug samples belong, prescribing volume and behavior). Prescribers 210 can also be selected via their Drug Enforcement Agency (DEA) number or individually by the brand manager 204. The DEA number is a unique global identifier that identifies a particular prescriber who prescribes drugs in the United States.

After the brand manager 204 has selected a group of prescribers 210, the brand manager 204 produces a set of brand rules 206 which define the availability of drug samples to each of the prescribers 210. The set of brand rules 206 may cause one prescriber's drug sample availability and characteristics to be different from those of another prescriber. Thus, for each prescriber there is a virtual drug sample cabinet tailored specifically for that prescriber. Preferably, the group of prescribers 210 is divided into segments. The brand rules provide personalization and customization for each segment. Many other personalization capabilities to tailor the distribution of drug samples to prescribers 210 are possible, such as various delivery methods; various drug strengths; trademark and local presentation of drug samples; customized drug disclaimers; specific product, package, and brand Web sites; and facilitating the scheduling of prescriber interactions with sales representatives or medical science liaisons.

The set of brand rules 206 are used to focus the drug sample fulfillment platform 208 to distribute drug samples to prescribers 210. The drug sample fulfillment platform 208 is preferably a Web-based platform that enables registered health care professionals, pharma 202's sales representatives, and other authorized users to order drug samples and obtain related drug information via the Internet. The drug sample fulfillment platform 208 is also preferably electronically linked to one or more prescriber-oriented online portals (such as Web MD), an e-Detailing service (such as Lathian's MyDrugRep.com), or to a prescriber's practice management software running on a computer system in the prescriber's office.

The drug sample fulfillment platform 208 is tailored based on the brand rules 206 established by the brand manager 204 for each drug and prescriber segment. Using the drug sample fulfillment platform 208, the brand manager 204 can select which prescribers are authorized to use the drug sample fulfillment platform 208 and the services provided thereon, the forms of drug samples they can access, and the drug sample quantity and delivery method. The drug sample fulfillment platform 208 can be configured to allow a prescriber to request a physical sample drop shipment. Requests for such physical samples are electronically communicated (including facsimile communications) to the brand manager 204's designated fulfillment vendors that pick, pack, and ship physical samples to the requesting prescriber's office. Using this method, prescribers 210 no longer need to rely on sales representatives to deliver physical samples. As an alternative to physical samples, the prescribers 210 use the drug sample fulfillment platform 208 to obtain pre-printed vouchers. These vouchers, when accompanied by a prescription, can be redeemed at a pharmacy 215 by patients 214 for free trial medication. The drug sample fulfillment platform 208 can be configured to allow prescribers 210 to request a drop shipment of pre-printed drug vouchers. If the brand rules 206 allow, prescribers 210 may print on demand coupons from the drug sample fulfillment platform 208. These on-line, on-demand print coupons are printed real-time in the prescriber's office. The prescriber signs the printed coupon as a prescription or attaches the voucher to a prescription for the patients 214 to redeem at the pharmacy 215 to obtain free drug sample medication. One advantage of both types of vouchers is that they ensure that the drug samples distributed to patients 214 are fresh, with their efficacy not diminished by expiration.

Figure 2A:
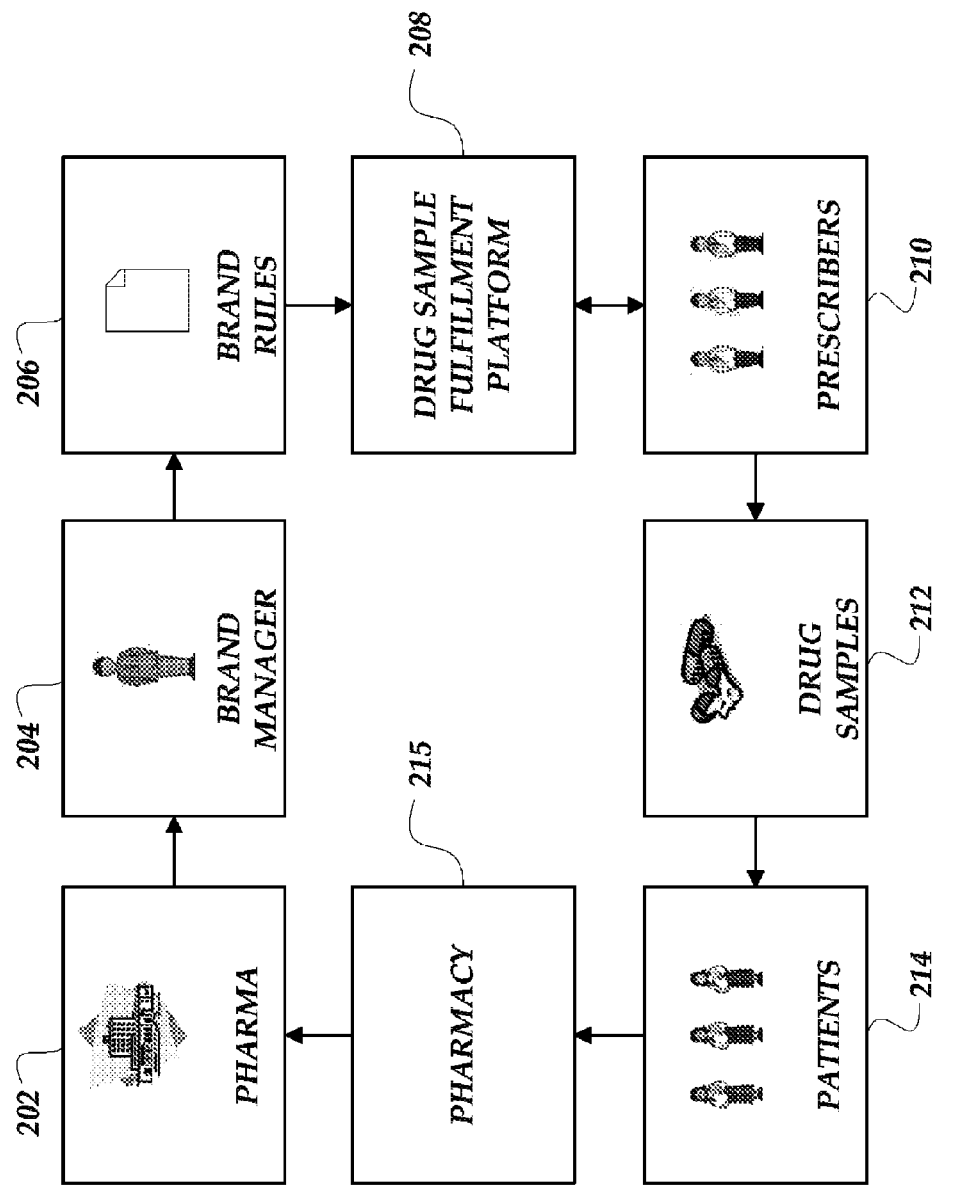
FIG. 2A is a block diagram illustrating an exemplary drug sampling fulfillment architecture.
Figure 2B:
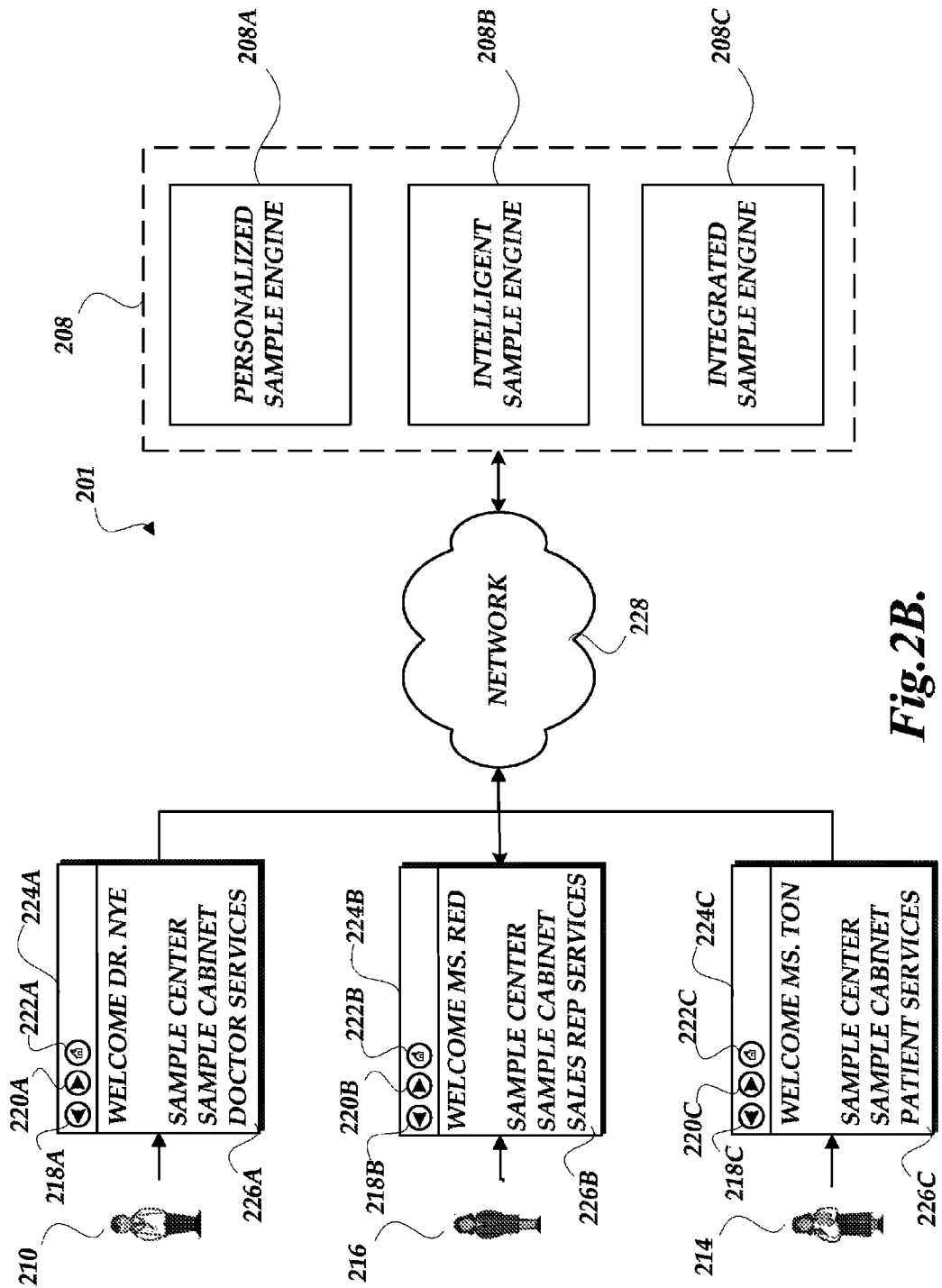
FIG. 2B is a block diagram illustrating pieces of a system for drug sample fulfillment distribution, according to one embodiment of the present invention.

FIG. 2B illustrates a system in which a prescriber 210, a sales representative 216, and a patient 214 interact with the drug sample fulfillment platform 208. This system is a networked computing environment that has pieces of hardware and software applications. The prescriber 210, the sales representative 216, and the patient 214 interact with the resources of the networked computing environment 200 via personal computers (not shown). A number of Web browsers 224A-224C run on personal computers. These Web browsers are software that let the prescriber 210, the sales representative 216, and the patient 214 view HTML documents and access files and software related to those documents on the drug sample fulfillment platform 208. Web browsers 224A-224C include a number of tools for navigation, such as BACK buttons 218A-218C; FORWARD buttons 220A-220C. These buttons are positions on navigation bars allowing easy access to Web pages by the prescriber 210, the sales representative 216, and the patient 214.

Web pages 226A-226C are each a starting point to a Web site that serves as a gateway to a collection of links, content, and services designed to guide the prescriber 210, the sales representative 216, and the patient 214 to information they are likely to find interesting that relates to drug samples and their distribution. Web pages 226A-226C include greetings that identify a particular user of the drug sample fulfillment platform 208, such as "WELCOME DR. NYE" for the prescriber 210; "WELCOME MS. RED" for the sales representative 216; and "WELCOME MS. TON" for the patient 214. Web pages 226A-226C include a hyperlink (SAMPLE CENTER), that allows access to available drug samples personalized to the particular user, and another hyperlink (SAMPLE CABINET), that allows access to the drug sample ordering history of the particular user. Hyperlinks "DOCTOR SERVICES," "SALES REP SERVICES," and "PATIENT SERVICES" of Web pages 226A-226C allow the prescriber 210, the sales representative 216, and the patient 214 to access drug information, answers to frequently asked questions, profile updates, and online drug sample information. Web pages 226A-226C and pieces of content on these Web pages are made available by the drug sample fulfillment platform 208 via a network 228. The network 228 is a group of computers and associated devices that are connected by communication facilities, such as the Internet.

The drug sample fulfillment platform 208 is one or more computers or one or more programs executing on one or more computers that respond to requests of a user, such as the prescriber 210, the sales representative 216, or the patient 214, to download Web pages 226A-226C and pieces of content associated with Web pages 226A-226C. In one embodiment, Web pages 226A-226C are preferably available as a response to an application specific messaging protocol. Web pages 226A-226B, as a response to an application specific messaging protocol, mate with a Web portal when the prescriber 210, the sales representative 216, or the patient 214 use the Web portal. The drug sample fulfillment platform 208 can push a message, such as via e-mail or a pop-up message, to the prescriber 210, when it notices that the prescriber 210 has not ordered a drug sample for a certain amount of time. Depending on the prescriber's order history, his specialty, etc., the message may be pushed to help remind the prescriber about the availability of drug samples.

In one embodiment, the drug sample fulfillment platform 208 comprises two engines, a pharma rules sample engine 208A (encompassing personalization and intelligent brand rule implementation), and a marketing sample engine 208C (encompassing integration with drug sample suppliers and Web portals). The pharma rules sample engine 208A tailors the distribution of drug samples to one or more prescribers 210, one or more sales representatives 216, and one or more patients 214. The pharma rules sample engine 208A monitors the distribution of drug samples to a particular user, such as the prescriber 210. If the prescriber 210 does not respond to the tailored drug sample allocation as specified by the pharma rules engine 208A, the pharma rules engine 208A modifies the allocation of drug samples to the prescriber 210 so that the prescriber 210 responds more favorably, such as by prescribing to his patients the distributed drug samples. If the prescriber 210 does not respond at all, the pharma rules sample engine 208A reduces or eliminates the allocation of drug samples to the prescriber 210. The marketing sample engine 208C links or integrates the supply of drug samples and parties who are interested in drug samples, such as the prescriber 210, the sales representative 216, or the patient 214. The combination of the two engines reduces or solves the problem of the lack or inconsistent supply of drug samples available for interested parties to prescribe or use.

Various embodiments of the present invention allow the sales representative 216 to access the drug sample fulfillment platform 208 to order physical samples or pre-printed vouchers to be shipped to the sales representative 216 for distribution. The sales representative 216 may have limited capacity to distribute many physical samples or massive amounts of pre-printed coupons. Instead, the sales representative 216 can access the drug sample fulfillment platform 208 to print a desired number of coupons to give to the prescriber 210. In one embodiment, to access the drug sample fulfillment platform 208, the sales representative 216 authenticates that she has the proper access by providing a territorial identifier in which she operates and her last name, among other pieces of information. Preferably, the number of coupons that the sales representative 216 can print in any one log-in session is limited to a certain quantity, as specified by the brand rules 206.

The drug sample fulfillment platform 208 can also serve as an avenue for consumers, such as the patients 214, to learn about available drugs and request samples.

Consumers can access the Web site and print vouchers for brand manager 204—approved drugs to take to their individual physician for signature or authorization. Thereby, consumers could be categorized as either: general consumer-individuals having public web access to a "general sample medicine cabinet"; or patient consumer-individuals with privileged access to a custom formulary program due to their health plan affiliation.

Figure 2C:
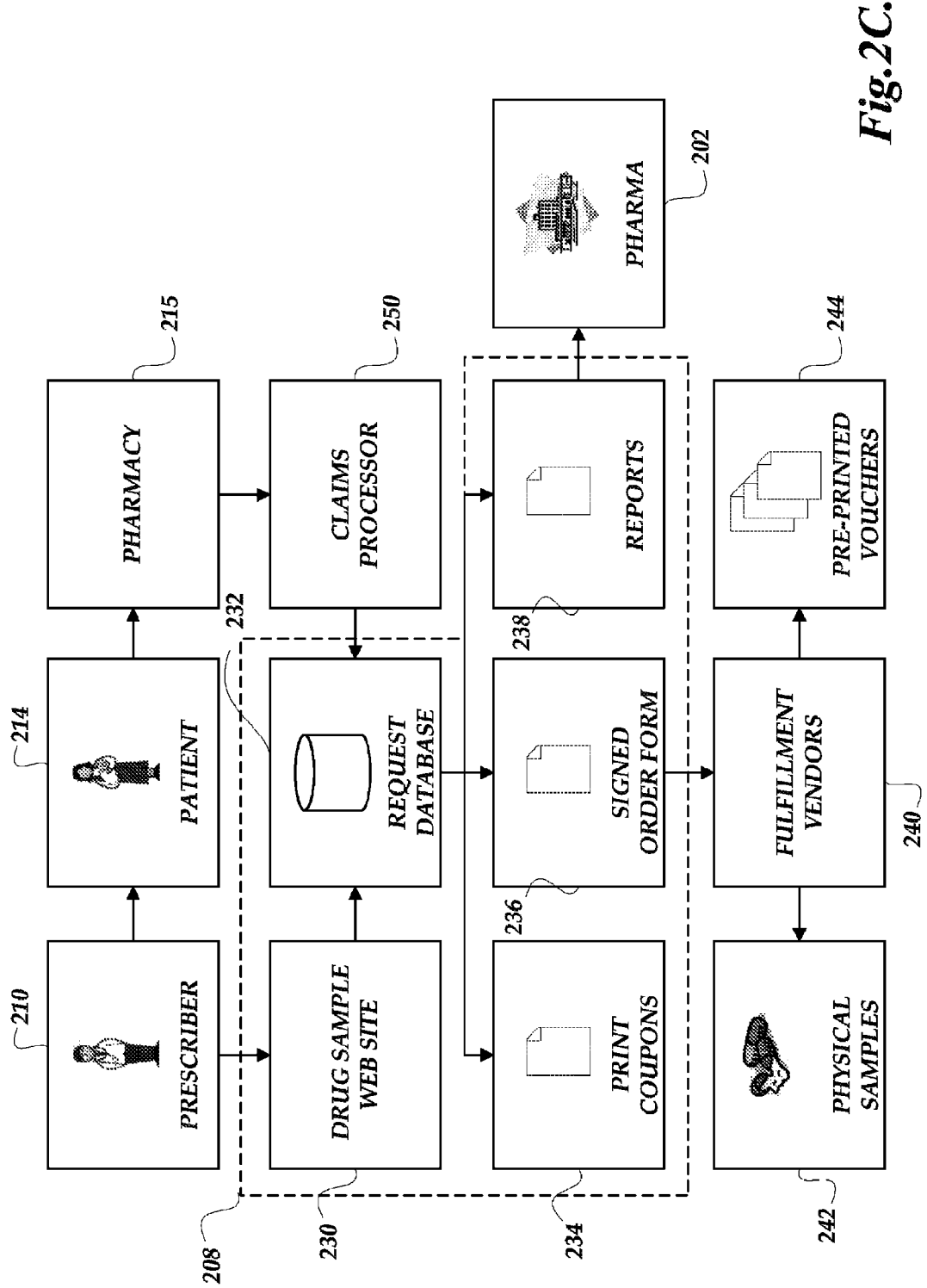
FIG. 2C is a block diagram illustrating pieces of a system for drug sample fulfillment distribution, according to one embodiment of the present invention.
Figure 4A:
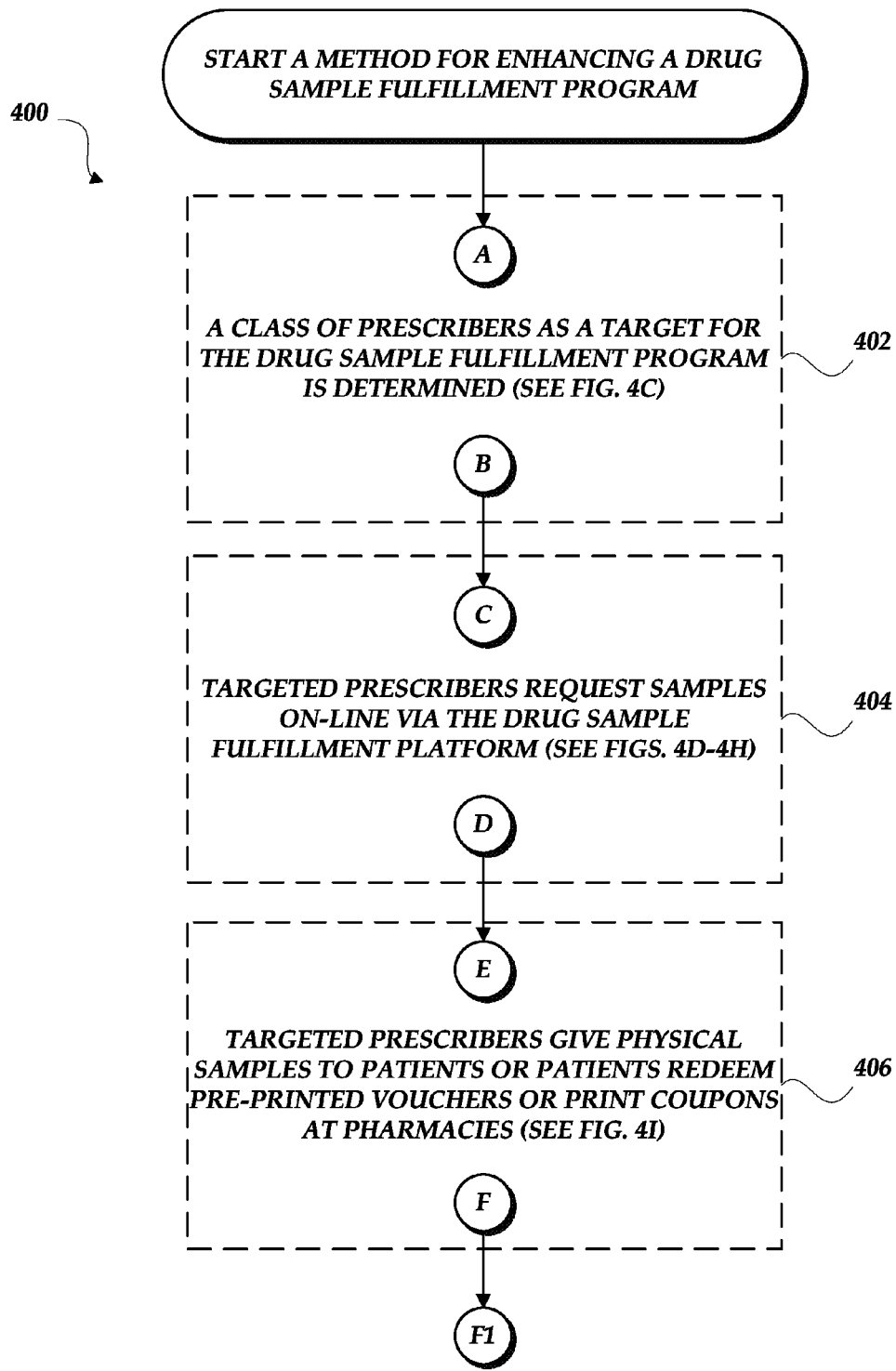
FIGS. 4A-4J are process diagrams illustrating a method for enhancing a drug sample fulfillment program, according to one embodiment of the present invention.
Figure 4B:
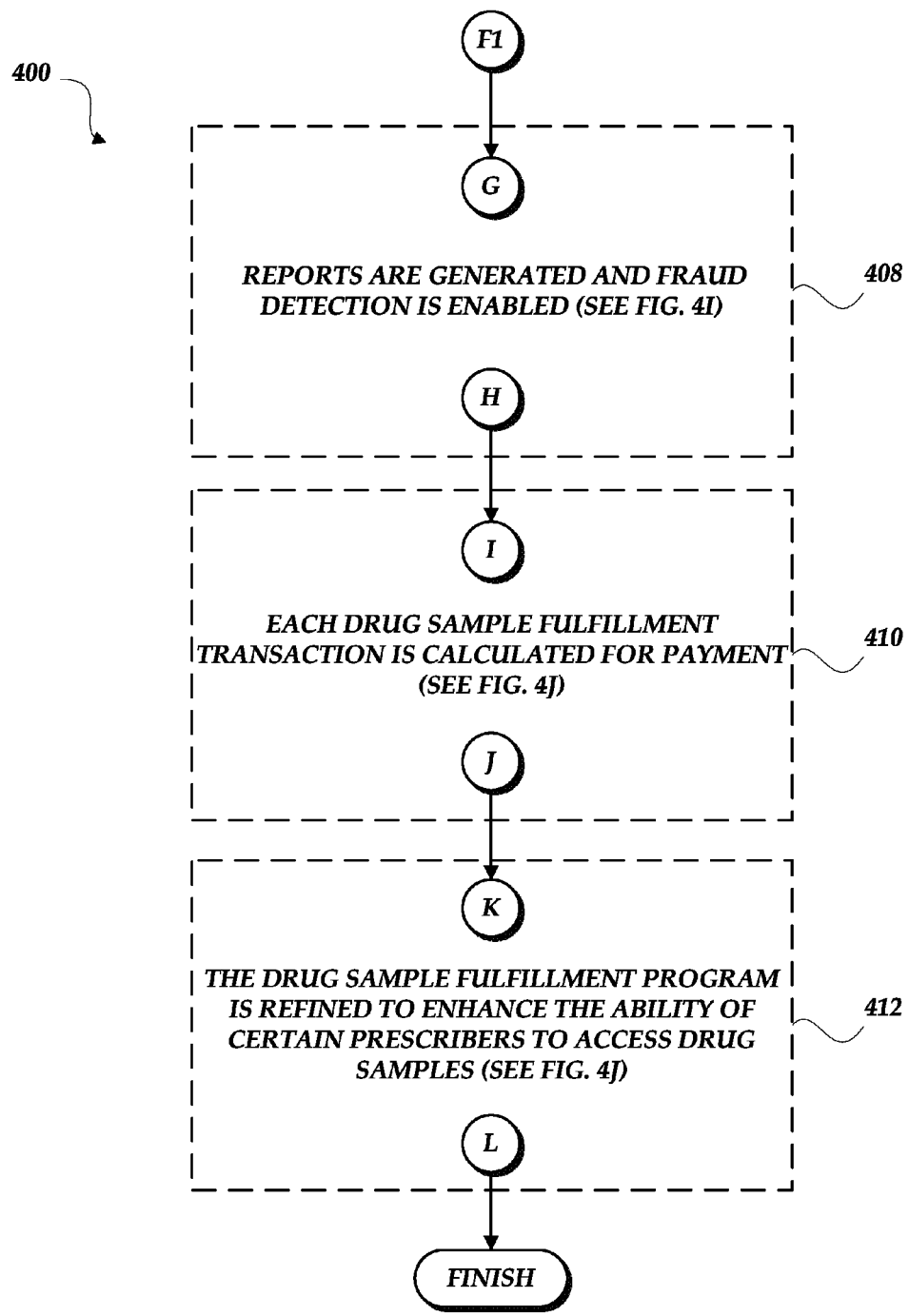
Figure 4C:
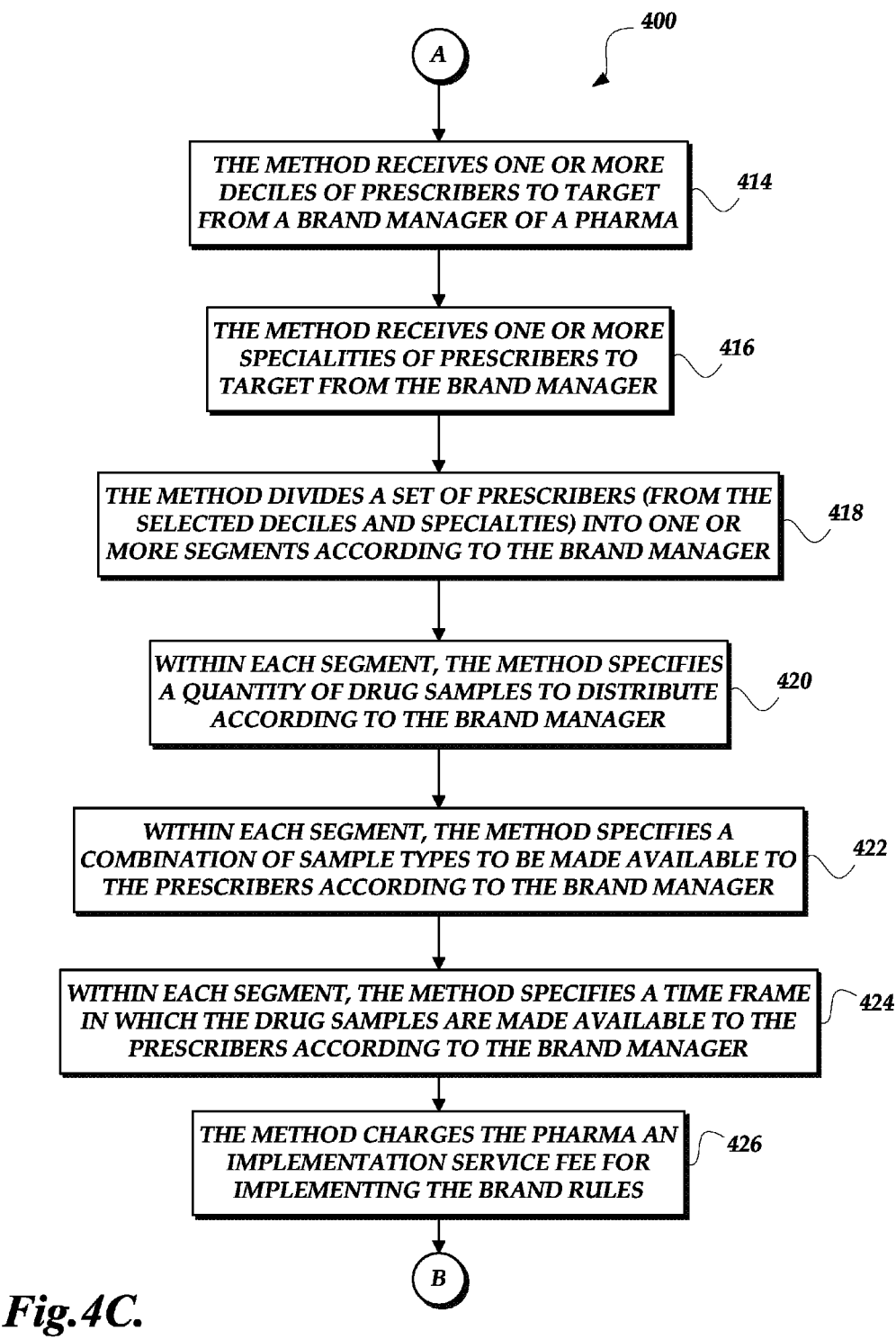
Figure 4D:
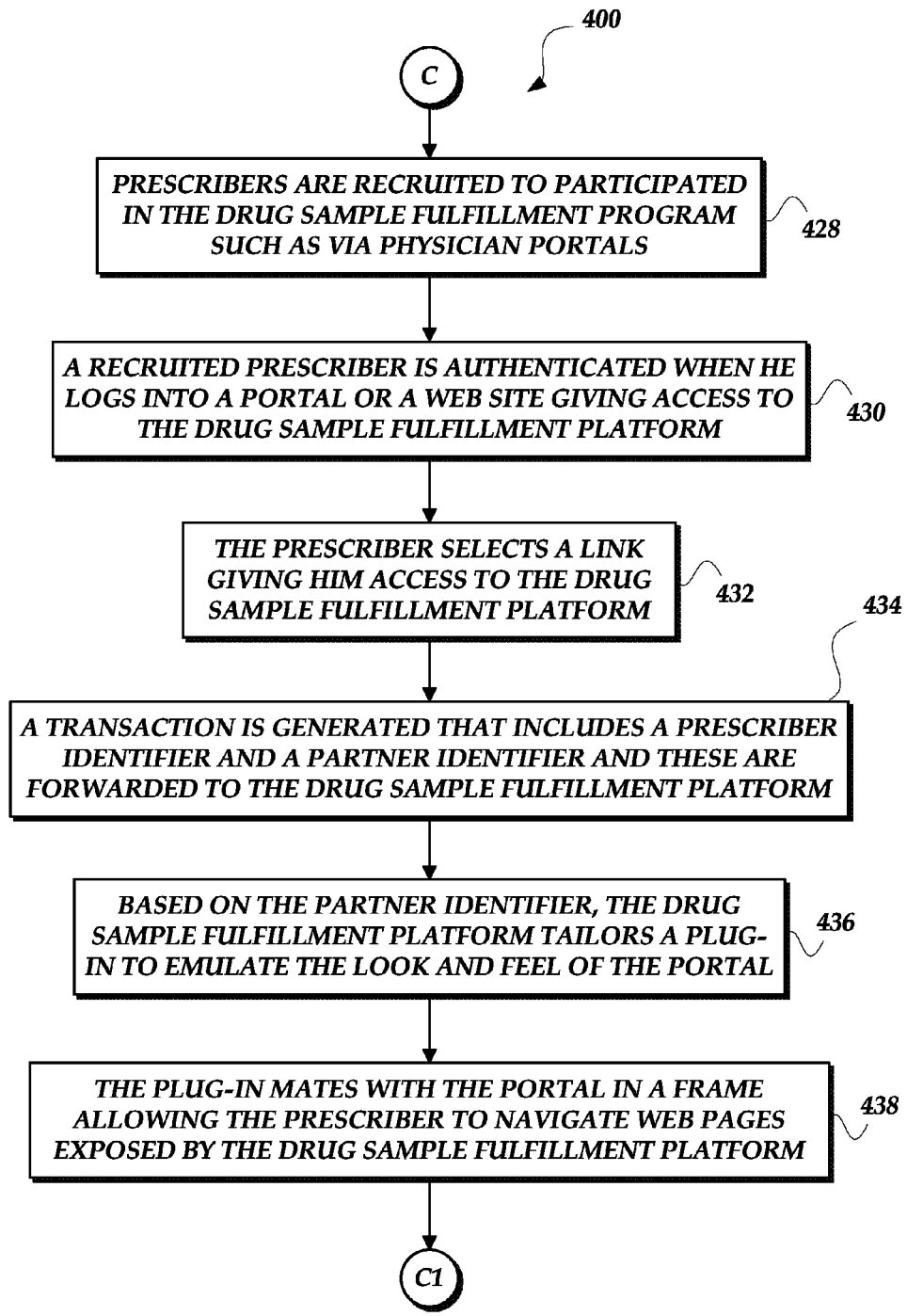
Figure 4E:
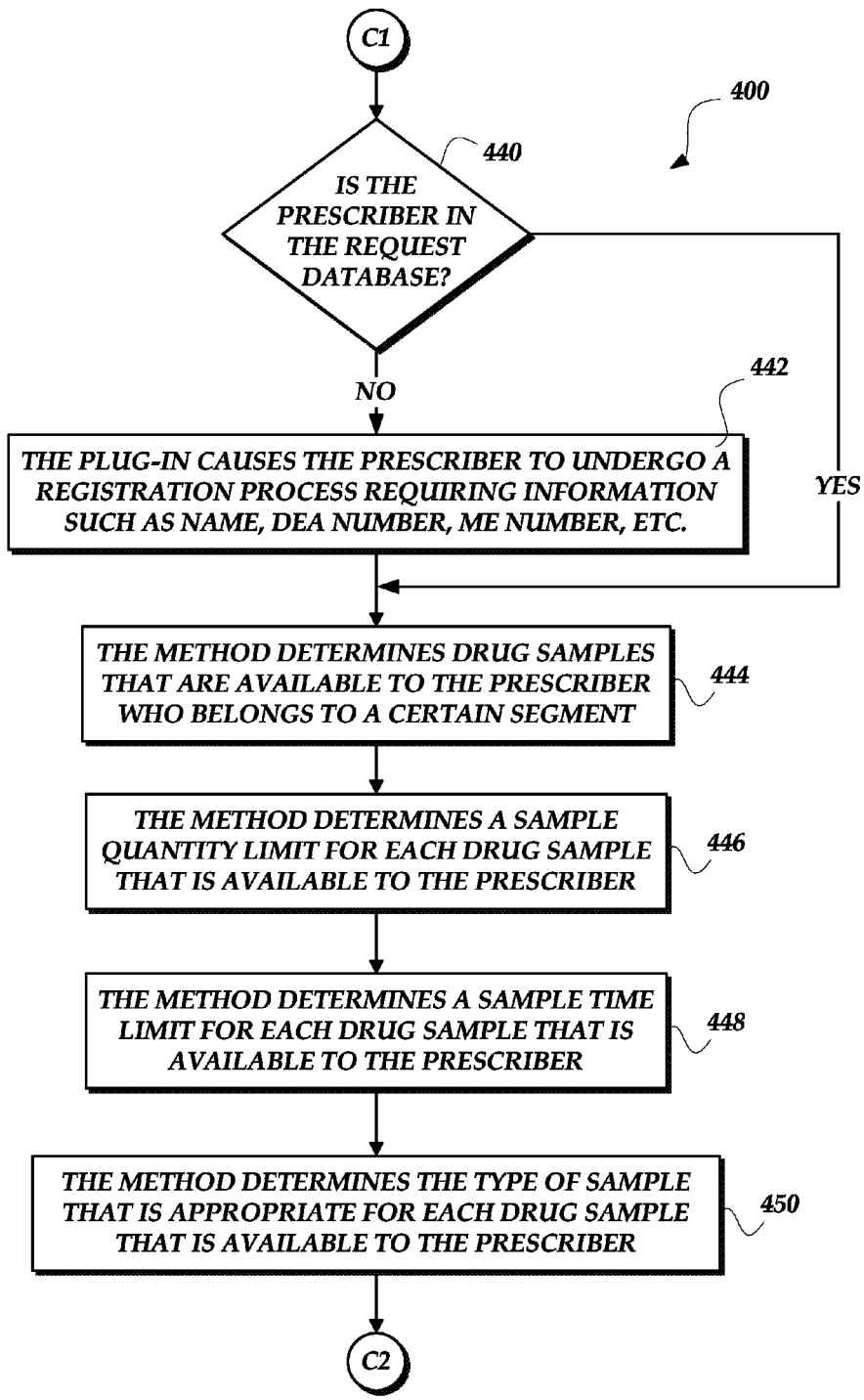
Figure 4F:
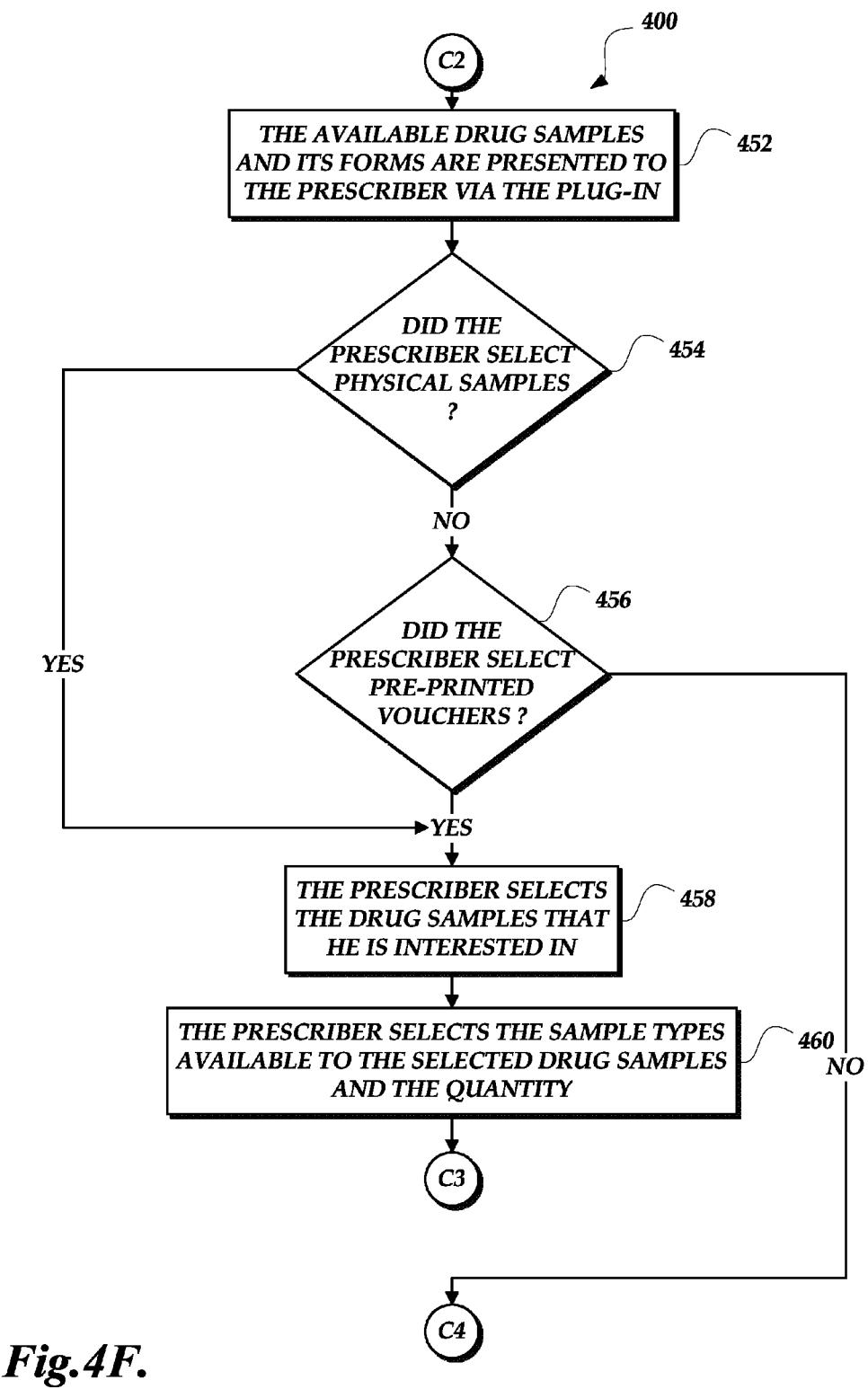
Figure 4G:
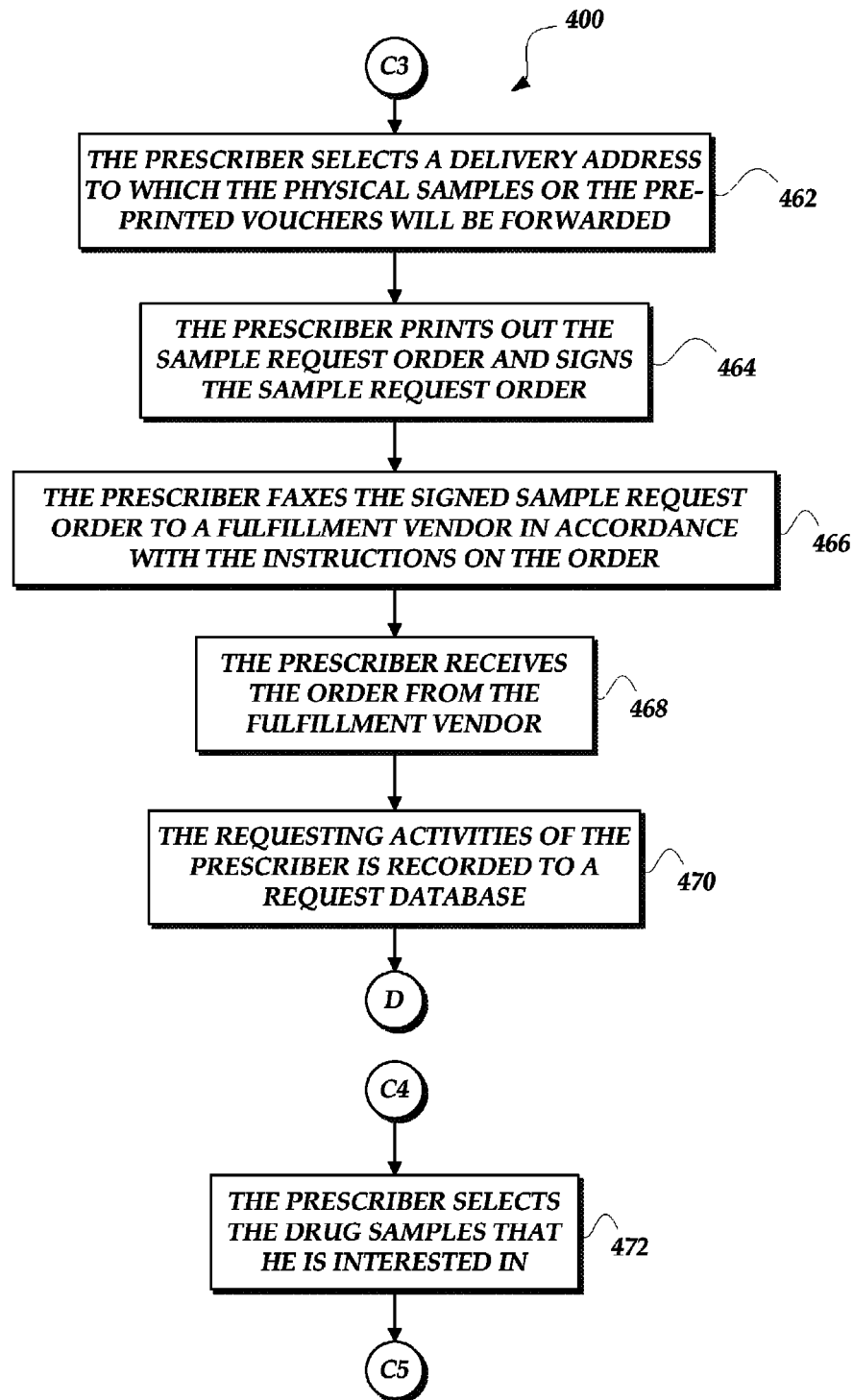
Figure 4H:
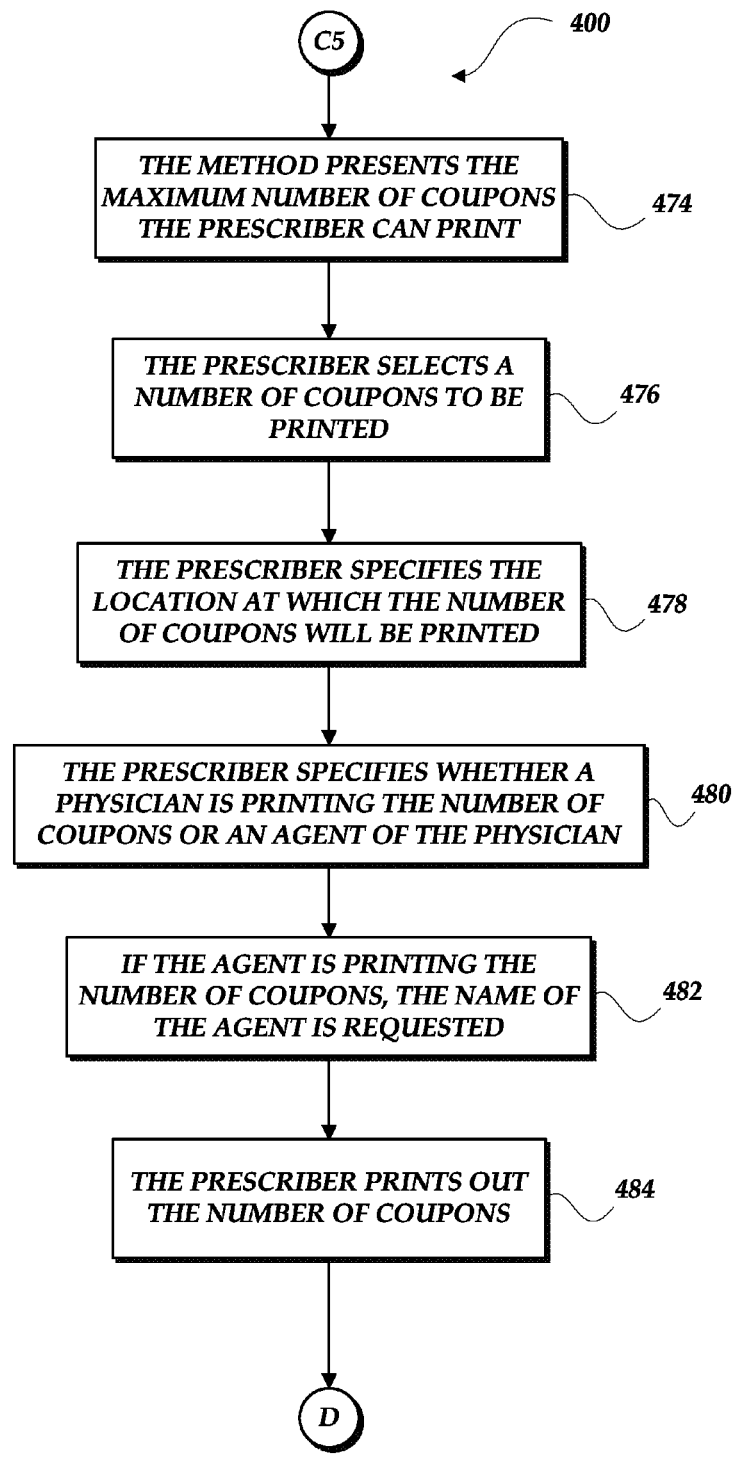
Figure 4I:
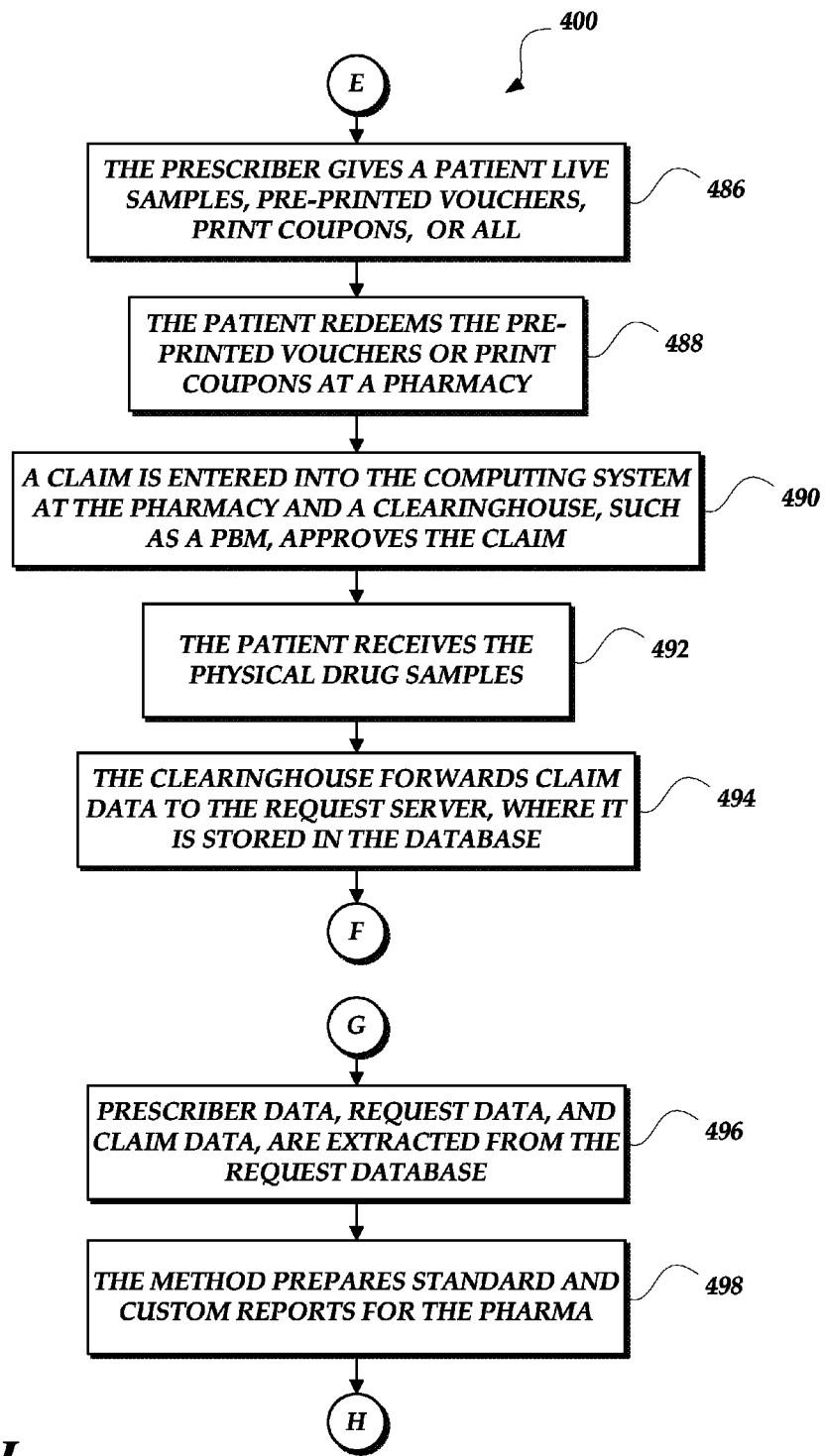
Figure 4J:
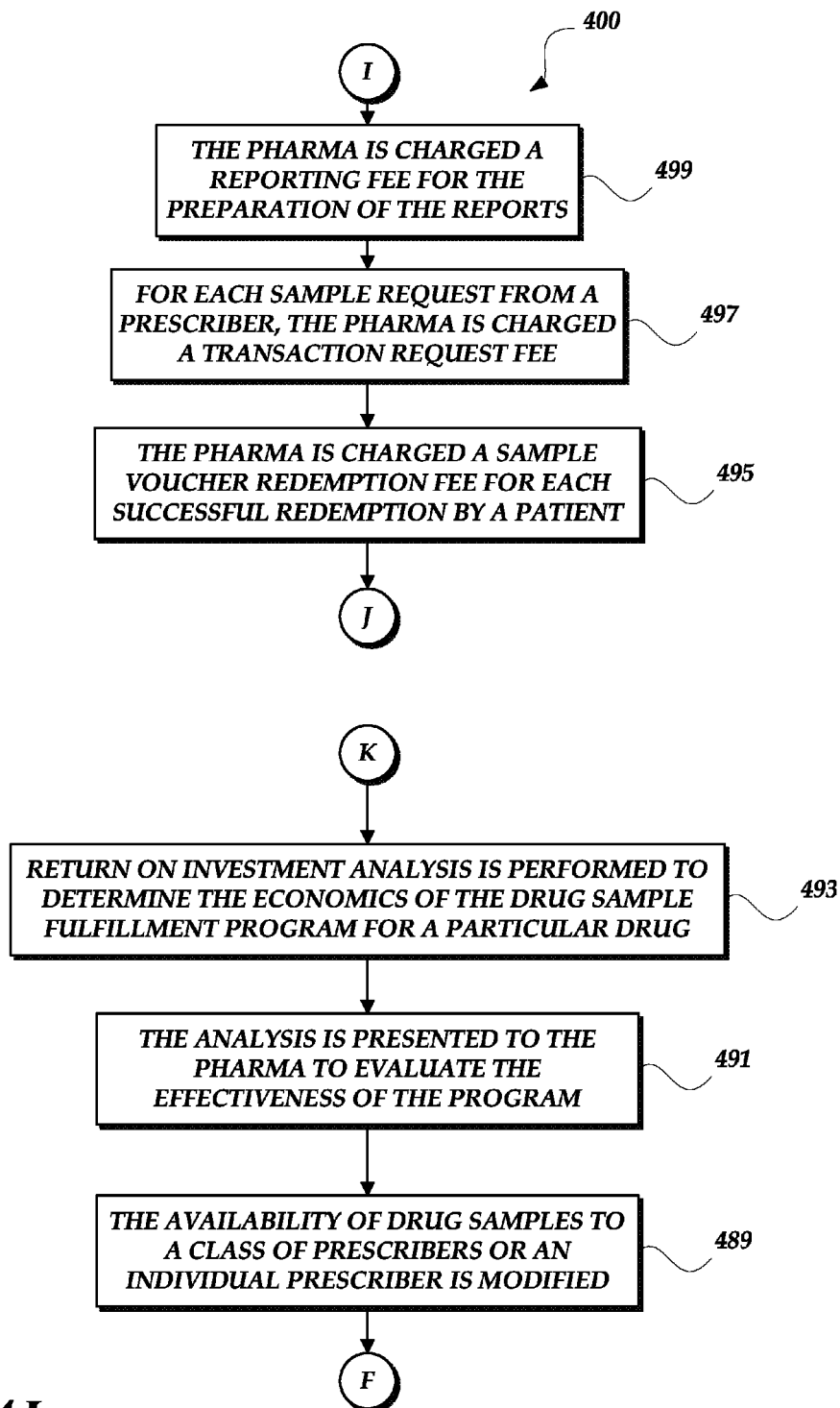

FIG. 2C illustrates another embodiment of the drug sample fulfillment platform 208. The prescriber 210 accesses a drug sample Web site 230 preferably via a Web portal. By selecting a link on the Web portal, the prescriber 210 generates a transaction that includes at least two pieces of information: a prescriber identifier and a partner identifier. The prescriber identifier uniquely identifies the prescriber 210 whereas the partner identifier identifies the Web portal from which the prescriber 210 selects the link to connect to the drug sample Web site 230.

The drug sample Web site 230 produces Web pages that conform to the look and feel of the Web portal with the particular partner identifier. The prescriber identifier will be used by the drug sample Web site 230 to consult with the request database 232 to determine whether the prescriber 210 has visited the drug sample Web site 230 before. If the prescriber identifier is not stored in the request database 232, then it is the prescriber 210's first visit to the drug sample Web site 230. The drug sample Web site 230 will cause the prescriber 210 to undergo a registration process. Among other information, the drug sample Web site 230 asks the prescriber 210 for his name, his individual DEA number, his work address, his medical state license number, his specialty, his e-mail address, his phone, his fax number, and whether the prescriber 210 desires to have his name forwarded to a partner Web site that may provide further drug information, among other pieces of information. The prescriber 210 need not provide all of these pieces of information, because the drug sample Web site 230 can communicate with the prescriber-oriented Web portal to pull various pieces of information already associated with the prescriber 210. This registration process is preferably run only once for a particular prescriber 210.

Once the prescriber 210 has registered with the drug sample Web site 230, the drug sample Web site 230 will generate a personalized list of drug samples that are available to the prescriber 210 to obtain. In terms of services that can be provided to prescribers in addition to requesting drug samples, prescribers can be provided with information with respect to drugs, continuing medical education, peer forums and conferences, and access to reports on adverse drug reactions from the Web sites of pharmaceutical companies, and from the FDA. Upon exiting the drug sample Web site 230, the prescriber 210 is returned to the Web page of the Web portal from which the prescriber 210 linked to the drug sample Web site 230. During registration, the prescriber 210 is asked to select whether he is interested in receiving future drug samples (via a therapeutic class interest survey) to treat an existing or a new therapeutic class. If he elects to receive future drug samples, when these drug samples become available the prescriber 210 will be notified when the prescriber 210 returns to the drug sample Web site 230.

The prescriber 210, depending on the brand rules 206 specified by the brand manager 204, can access a combination of three sample forms including physical samples 242, pre-printed vouchers 244, and print coupons 234. The physical samples 242 are drug samples that are pre-packaged by the pharma 202 and shipped by a single brand manager-designated fulfillment vendor 240. The prescriber 210 can also order pre-printed vouchers 244, which are pre-printed pads of coupons. These coupons are picked, packed, and shipped to the prescriber 210 via the fulfillment vendors 240 (which may or may not be the same vendor which distributes physical samples). The print coupons 234 are those coupons that prescriber 210 prints in his office. The prescriber 210 can then sign the coupon and give the signed coupon to the patient 214.

To obtain either physical samples 242 or pre-printed vouchers 244, the prescriber 210 prints an order form from the drug sample Web site 230 via the request database 232, signs the order form, and faxes it to one or more fulfillment vendors 240. The pharma 202 can specify a fulfillment vendor 240 (whose fax number is printed on the order form) to which the prescriber 210 faxes the signed order form to obtain physical samples 242 and/or of pre-printed vouchers 244 as applicable. The order form 236 is first presented electronically to the prescriber 210 for the prescriber 210 to specify different drug samples that he is interested in. The order form 236 is also personalized to a particular prescriber 210 and a particular fulfillment vendor 240 in accordance with brand rules 206.

The drug sample fulfillment platform 208 is designed to work with any contracted prescriber-oriented Web portal which the prescriber 210 may use and any fulfillment vendor 240 that the pharma 202 wishes to work with via an application specific messaging protocol. The prescriber 210 may order drug samples that may have to be fulfilled by two fulfillment vendors 240. The drug sample Web site 230 manages such a situation by printing one order form to be faxed to a particular fulfillment vendor and another order form to be faxed to a second fulfillment vendor. The drug sample fulfillment platform 208 removes the complexity of ordering drug samples for the prescriber 210 while reducing or eliminating mistakes (e.g., errors due to unreadable handwriting). Even if the signed order form 236 is somehow misplaced or lost, the prescriber 210 can print it out again (via the history reprint function) from the drug sample Web site 230 and fax the signed order form to the fulfillment vendors 240 to obtain the desired drug samples.

Upon receiving physical samples 342, pre-printed vouchers 244, or print coupons 234, the prescriber 210 can provide a combination of those sample forms to the patient 214 to redeem for free medications at the pharmacy 215. When the patient 214 comes to the pharmacy 215 to redeem sample forms for drug samples, the pharmacy 215 forwards the claim to a claims processor 250. The claims processor 250 decides whether to approve the claim. If the claim is approved, the pharmacy 215 provides the desired drug samples to the patient 214 free of charge.

The request database 232 stores for each prescriber 210 identification and the quantity of drug samples that were ordered. The drugs and quantity ordered is compared with the allocation limits for a particular prescriber. This can be presented to the prescriber 210 via the drug sample Web site 230 so that the prescriber 210 knows how many more drug samples the prescriber 210 can order. These pieces of information, among others, are stored by the request database 232. The information in the database can be correlated when the patient 214 takes a pre-printed voucher 244 or a print coupon 234 and redeems it at the pharmacy 215. These pieces of information can be analyzed and explained to the pharma 202 via one or more reports 238. For example, suppose a print coupon was redeemed on a particular date by the patient 214. The reports 238 can indicate when the coupon was redeemed by the patient 214. Moreover, the reports 238 can show whether there is a correlation between a drug sample fulfillment distribution program as specified by the brand rules 306 and the prescribing trend of the prescriber 210.

Various exemplary Web pages comprising the drug sample Web site 230 are illustrated at FIG. 3A and FIG. 3B. Web pages 302A-302E are navigated by a set of application built navigational buttons/links/tabs, such as PREVIOUS/CANCEL buttons 304A-304E, NEXT/CONTINUE/CONFIRM buttons 306A-306F, and HOME buttons 308A-308F. These buttons appear in standard locations on Web pages 302A-302E throughout the application. Regarding the Web page 302A, a greeting 314 "WELCOME NORMAN SMITH, M.D." identifies the prescriber 210. A set of "SAMPLE CENTER" links 316 allows the prescriber 210 to access various sample services, such as "REQUEST SAMPLES" and "PRINT COUPONS." A set of "MY SAMPLE CLOSET" links 318 allows the prescriber 210 to review his order history. A set of "PHYSICIAN SERVICES" links 320 allows the prescriber 210 to access drug data, get answers to frequently asked questions, update his profile, request additional detail support or product information from pharma sales representatives 106, obtain product information online, and therapeutic class survey. A further service available through various embodiments of the present invention includes maintaining "MY SAMPLE CLOSET" for a prescriber. Particular drug products and quantities can be suggested to the prescriber, and then the sample drug closet can be automatically replenished as requested by the prescriber. Also, for sample programs that expire, the system can shut down redemptions through the pharmacy network via the claims processor 250, notify all participating prescribers, and disable all online sample order requests for the specific drug.

Selecting the "REQUEST SAMPLES" link of the set of links 316 brings up an exemplary Web page 302B for the prescriber 210 to request drug samples. A title of the Web page "REQUEST SAMPLES" 312A appears on the menu bar and is flushed to the left for both the Web page 302B as well as the Web page 302C. Regarding the Web page 302B, line 322 identifies the name of the prescriber 210. Area 324 is an array formed from four columns and a number of rows. The first column identifies the product or the drug sample available to the prescriber 210. The second column is the sample type for a particular drug that the prescriber 210 can order. The third column identifies the form in which the drug sample is made available. The fourth column identifies the quantity that the prescriber 210 specifies. The first row of the area 324 indicates that "DRUG A" is available in physical form (or in an alternative form such as pre-printed vouchers) for which there are five samples in a box and that the prescriber 210 has ordered a quantity of one. The second column specifies that the "DRUG B" is available via pre-printed forms (or in an alternative form such as physical samples) for which 40 coupons are available in a pad and that the prescriber 210 has ordered a quantity of two. The third column specifies that drug C is available in physical form (or in an alternative form such as pre-printed vouchers) for which there are 30 samples in a box and that the prescriber 210 has ordered a quantity of five.

The prescriber 210 may select a button 326 "ADD MORE PRODUCTS" to add more drug samples to be ordered. The prescriber 210 also specifies a delivery location at line 328 for which "BELLTOWN" has been selected (other delivery destinations may be possible). When the prescriber 210 is satisfied with the order, he selects a CONTINUE button 329 to prepare a finalized order form for printing, which is presented by the Web page 302C. A PRINT button 310A is available for the prescriber 210 to select to print the finalized order form. Line 330 indicates an order number "NN1" and a placement date "Apr. 24, 2003," among other pieces of information. An area 332 is a recap of the area 324 which shows the various drug samples that the prescriber 210 is interested in and the quantity of each that the prescriber 210 is expecting to receive. Area 334B requires the prescriber's signature as well as an execution date of the order form. Area 336 indicates the delivery address to which the samples will be shipped when the order form has been processed by fulfillment vendors 340.

If the prescriber 210 selects the "PRINT COUPONS" link in area 316 of the Web page 302A, the Web page 302D appears. Line 338 identifies the name of the prescriber 210, which is "NORMAN SMITH, M.D." An area 340 includes a link "I HAVE READ AND AGREE TO TERMS . . . ." which allows the prescriber 210 to select and review terms and conditions for printing coupons for certain drug samples. The prescriber must check the box indicating his agreement with the PDMA (Prescription Drug Marketing Act which is a federal regulation prohibiting among other things the copying and/or selling of drug sample vouchers or coupons) guidelines before being allowed to print. The area 340 includes a "PRODUCT" line identifying the drug (DRUG A) for which the prescriber 210 may print coupons. An "Important Information" line specifies important information that the prescriber 210 can review in connection with the selected drug sample. An "INTENT TO PRINT NUMBER" line specifies the number of coupons which the prescriber 210 wishes to print. A "LOCATION" line allows the prescriber 210 to specify the prescriber's address that will be printed on the voucher. A "WHO" line allows the prescriber 210 to specify whether the prescriber 210 is a physician or an agent of the physician. A "NAME" line allows the person printing the coupons to specifically identify herself if she is an agent of the prescriber. Selecting a CONTINUE button 341 brings forth the Web page 302E for the prescriber 210 to review. Selecting a CANCEL button 343 terminates the session.

The content of the Web page 302E is in essence a coupon for the prescriber 210 to dispense to the patient 214. A PRINT button 310B allows the prescriber 210 to select and print out one or more coupons as specified on the Web page 302D. Line 342 allows the prescriber 210 to cancel the printing process. Line 344 identifies the names of the prescriber "NORMAN SMITH M.D." and the drug "DRUG A" to be redeemed by the printed coupon. Line 346 identifies a patient name. Line 348 contains the date that the coupon is given to the patient 214, a carrier number "23" and a group ID number "9" associated with the claim when the coupon is presented at the pharmacy 215. Line 350 identifies the drug to be redeemed by the coupon. Line 352 indicates the dosage. Additionally, an expiration date "May 24, 2000" is specified on line 352 (a rolling voucher expiration date from date printed or a fixed date as defined by pharma brand rules 206). Line 354 provides space for the prescriber's signature, and the prescriber's DEA number is shown next to an area where the prescriber writes his signature. Further, the printed voucher can be customized by the prescriber to include or not include his office phone number and DEA number.

FIGS. 4A-4L illustrate a method 400 for enhancing a drug sample fulfillment program. For clarity purposes, the following description of the method 400 makes references to various elements illustrated in connection with the drug sample fulfillment platform 208 (FIGS. 2A, 2B, 2C), brand rules 206 (FIG. 2A), the drug sample Web site 230 (FIG. 2C), and Web pages 302A-302E (FIGS. 3A-3B). From a start block, the method 400 proceeds to a set of method steps 402, defined between a continuation terminal ("Terminal A") and an exit terminal ("Terminal B"). The set of method steps 402 describes the commencement of the drug sample fulfillment program by determining a class of prescribers as a target for the drug sample fulfillment program.

From Terminal A (FIG. 4C), the method 400 proceeds to block 414 where the method receives one or more deciles of prescribers to target from the brand manager 304 of the pharma 302. The method 400 also receives one or more criteria to target eligible prescribers as determined by the brand manager 204. See block 416. The method then divides a set of prescribers (from the selected deciles and specialties) into one or more segments according to the brand manager 204. See block 418. At block 420, within each segment, the method 400 specifies a quantity of drug samples to distribute according to the brand manager 204. Next, at block 422, within each segment, the method 400 specifies a combination of sample types or forms (i.e., physical samples, pre-printed vouchers, or print coupons) to be made available to the prescribers 210 according to the brand manager 204. See block 422. Within each segment, the method 400 also specifies a time frame in which the drug samples are made available to the prescribers 210 according to the brand manager 204. See block 424. The method then charges the pharma 202 an implementation service fee for implementing the brand rules as set forth by the brand manager 204. See block 426.

Pharmaceutical companies and their sales representatives have certain rules that they use in determining that prescribers are to be given drug samples in general, as well as which drug samples are to be made available, and the quantity of such drug samples. These rules are established on a prescriber-by-prescriber basis and are in effect when a prescriber requests drug samples. Such rules can be based on many factors, including the specialty of the prescriber, the prescriber's location, the prescriber's age, the prescriber's past history of requesting drug samples and providing such samples to patients, and the prescriber's history in prescribing such drugs. When a prescriber's practice or situation changes, the rules for the prescriber with respect to drug samples provided can also be altered. From here, the method 400 enters the exit Terminal B.

From the exit Terminal B (FIG. 4A), the method 400 proceeds to a set of method steps 404, defined between a continuation terminal ("Terminal C") and an exit Terminal ("Terminal D"). The set of method steps 404 describes the ways in which targeted prescribers 210 request drug samples on-line via the drug sample fulfillment platform 208.

From Terminal C (FIG. 4D), the method 400 proceeds to block 428 where prescribers 210 are recruited to participate in the drug sample fulfillment program via prescriber-oriented portals, prescriber recruiting services, and/or e-Detailing providers. Other suitable recruitment techniques are possible, such as by telephone or fax. A recruited prescriber 210 is authenticated when he logs into a portal or a Web site giving access to the drug sample fulfillment platform 208. See block 430. This prescriber 210 selects a link on the portal giving him access to the drug sample fulfillment platform 208.

See block 432. A transaction is generated when the link is selected that includes a prescriber identifier and a partner identifier and these are forwarded to the drug sample fulfillment platform 208. See block 434. Based on the partner identifier, the drug sample fulfillment platform 208 tailors the Web pages in to emulate the look and feel of the prescriber-oriented portal. See block 436. The application specific messaging protocol allows the prescriber-oriented portal to open the sample fulfillment platform 208 within a frame allowing the prescriber 210 to navigate Web pages. See block 438. The method then enters another continuation terminal ("Terminal C1").

From Terminal C1 (FIG. 4E), the method 400 proceeds to decision block 440 where a test is made to determine whether the prescriber 210 is in the request database 232. If the answer to the test at decision block 440 is NO, the method 400 proceeds to block 442 where the drug sample fulfillment platform 208 causes the prescriber 210 to complete a registration process requiring information such as name, DEA number, medical state license number, etc. The method 400 proceeds next to block 444. If the answer to the test at decision block 440 is YES, the method 400 also enters block 444. The method 400 determines drug samples that are available to the prescriber (who belongs to a certain segment of prescribers). See block 444. At block 446, the method 400 determines a sample quantity limit for each drug sample that is available to the prescriber 210. At block 448, the method 400 determines a sample time limit for each drug sample that is available to the prescriber. For example, a particular drug is available to a prescriber for a limited duration beyond which he cannot order more. Next, the method 400 determines the type or form of sample that is appropriate for each drug sample that is available to the prescriber 210. See block 450.

Various embodiments of the present invention can also take into consideration certain preferences of a prescriber, such as printing DEA and/or office telephone numbers on the print on-demand voucher. The method 400 then enters another continuation terminal ("Terminal C2").

From Terminal C2 (FIG. 4F), the available drug samples and its forms are presented to the prescriber 210 via an application specific messaging protocol. See block 452. Next, at decision block 454, a test is made to determine whether the prescriber selected physical samples. If the answer is NO, another test is made at decision block 456 where it is determined whether the prescriber 210 selected pre-printed vouchers. If the answer to the test at decision block 454 or 456 is YES, the method 400 enters block 458. The prescriber 210 selects the drug samples that he is interested in on the Web page 302B. See block 458. Next, at block 460, the prescriber 210 selects the sample types (physical samples or pre-printed vouchers) available for the selected drug samples and quantity. See Web page 302B. The method 400 enters another continuation terminal ("Terminal C3").

If the answer to the test at decision block 456 is NO, the method 400 enters another continuation terminal ("Terminal C4").

From Terminal C3 (FIG. 4G), the method 400 proceeds to block 462 where the prescriber 210 selects a delivery address to which the physical samples or the pre-printed vouchers will be sent. See Web page 302B. The prescriber prints out the sample request order and signs the sample request order in one embodiment. In another embodiment, he need not sign the sample request order if it is for pre-printed vouchers 244. See block 464 (see also the Web page 302C). Next, at block 466, the prescriber 210 faxes the signed sample request order 236 to a fulfillment vendor 240 in accordance with the instructions on the sample request order 236. The prescriber 210 receives the order from the fulfillment vendor 240. See block 468. The requesting activities of the prescriber 210 are then recorded in the request database 232. The method 400 then enters the exit Terminal D.

From Terminal C4 (FIG. 4H), the method 400 proceeds to block 472 where the prescriber 210 selects the drug samples for which he is interested in printing out coupons. The coupons that are printed by the prescriber are dynamically built at the time requested so as to include the prescriber's name and address, the particular drug requested, the strength of the drug, the expiration date of the voucher, the prescriber's DEA number, and the trademark and logo not only of the drug, but also of the drug manufacturer. The method 400 then enters another continuation terminal ("Terminal C5").

From Terminal C5 (FIG. 4I), the method 400 proceeds to block 474 where the method 400 presents the maximum number of coupons the prescriber can print. The prescriber selects the number of coupons to be printed. See block 478 (see also the Web page 302D). The prescriber 210 then specifies whether a physician is printing coupons or whether an agent of the physician is printing them. See block 480 (see also the Web page 302D). If the agent is printing the coupons, the name of the agent is requested by the method 400. See block 482. The prescriber then prints out the number of coupons. See block 484. The method 400 then enters the exit Terminal D. From the exit Terminal D (FIG. 4A), the method 400 proceeds to a set of method steps 406, defined between a continuation terminal ("Terminal E") and an exit terminal ("Terminal F"). The set of method steps 406 describes the act of giving physical samples to patients by targeted prescribers 210 or patients 214 redeeming pre-printed vouchers or print coupons at pharmacies.

From Terminal E (FIG. 4J), the prescriber 210 gives the patient 214 physical samples, pre-printed vouchers, print coupons, or all of these. See block 486. The patient 214 redeems the pre-printed vouchers or print coupons at the pharmacy 215. See block 488. A claim is entered into the computer system at the pharmacy 215, and a clearinghouse, such as a pharmacy benefit manager, approves the claim. See block 490. If the claim is approved, the patient 214 receives the physical samples for free. See block 492. The clearinghouse then forwards claim data to the request database 232, where it is stored for later analysis. See block 494. The method 400 then enters the exit Terminal F.

From Terminal F (FIG. 4A), the method 400 proceeds to another continuation terminal ("Terminal F1"). From Terminal F1 (FIG. 4B), the method 400 proceeds to a set of method steps 408, defined between a continuation terminal ("Terminal G") and an exit terminal ("Terminal H"). The set of method steps 408 describes the commencement of the generation of reports and fraud detection is enabled.

From Terminal G (FIG. 4K), the method 400 proceeds to block 496, where the prescriber data, the request data, and the claim data are extracted from the request database 232. See block 496. The method 400 then proceeds to block 498 where the method 400 prepares standard and custom reports for the pharma 202. There are three types of reports that are possible. One report lists sample demand statistics. For example, the number of drug samples requested by a certain prescriber can be reported. As another example, the number of vouchers or coupons that were redeemed by patients of a particular prescriber can also reported. The second type of report provides promotional response analysis. For example, the correlation of the requested drug samples and the prescribing behavior of a particular prescriber is described. The third type of report focuses on return on investment analysis. For example, the pharma 202 spends a certain amount of money in connection with the drug sample fulfillment program managed by the brand manager 204. The number of prescriptions for the same drug by a certain prescriber can be correlated with the spending of the pharma 202 to generate potential return on investment analysis.

Through the process described above, certain information is captured, including the name of the prescriber, the date of the redemption of the coupon, the identity of the drug sample given, as well as certain information about the patient, but without identifying the patient. This information is made available to the pharma 202 so that vouchers and coupons for sample medications distributed by prescribers can be tracked. The pharma 202 can also obtain information as to the prescribing of the drug in question by a prescriber through the request database 232. In this manner, the pharma 202 can evaluate the effectiveness of providing drug samples to a prescriber, including how often the prescriber prescribes that same drug. This enables the pharma 202 to make determinations, including not only the success of its sample program generally, but also with respect to continuing to make samples of the drug available to the prescriber. The reported information can also be used to identify prescribers who would be good targets for new drugs being introduced by pharmaceutical companies or good candidates for drug focus groups, as well as perhaps for other products and services of interest to prescribers. Lastly, these reports can be utilized by sales representatives for the purpose of generating and distributing sample vouchers to their targeted prescriber clientele.

The information generated in these reports also aids in fraud analysis. For a given prescriber, an allocation limit for drug samples associated with that prescriber is known. Moreover, the time frame in which those drug samples are valid is also known and specified in the brand rules 206 by the brand manager 204. Based on the redemptions that come in via the claim data provided by the claim processor 250, fraud analysis can determine whether more vouchers or coupons were redeemed within the time frame limit than had been allocated. If there is an inconsistency between the allocation limit and the number of redeemed vouchers or coupons by patients, a flag is raised for further investigation. Preferably, the pre-printed vouchers and print coupons contain the prescriber's DEA number or other identifying indicia for accurate fraud detection analysis. The method 400 then enters the exit Terminal H.

From Terminal H (FIG. 4B), the method 400 proceeds to a set of method steps 410, defined between a continuation terminal ("Terminal I") and an exit terminal ("Terminal J"). The set of method steps 410 describes the payment calculation for each drug sample fulfillment transaction.

From Terminal I (FIG. 4L), the method 400 proceeds to block 499, where the pharma 202 is charged a reporting fee for the preparation of the reports generated in the set of method steps 408. For each request for a sample from a prescriber, the pharma 202 is also charged a transaction request fee. See block 497. The pharma 202 is also charged a sample voucher redemption fee for each successful redemption of a print coupon or a pre-printed voucher by the patient 214. See block 495. Not shown is an annual fee charged to the pharma 202 for the use of the drug sample fulfillment platform 208 and the maintenance of the drug sample fulfillment platform 208. Software updates as well as customization of various brand rules specified by the brand manager fall under this fee. The method 400 then enters the exit Terminal J.

From Terminal J (FIG. 4B), the method 400 proceeds to a set of method steps 412, defined between a continuation terminal ("Terminal K") and an exit terminal ("Terminal L"). The set of method steps 412 describes the commencement of the refining of the drug sample fulfillment program to enhance the ability of certain prescribers 210 to access drug samples.

From Terminal K (FIG. 4M), the method 400 proceeds to block 493 where a return on investment analysis is performed to determine the economics of the drug sample fulfillment program for a particular drug. The analysis is then presented to the pharma 202 to evaluate the effectiveness of the program. See block 491. The availability of drug samples to a class of prescribers 210 or an individual prescriber is then modified. See block 489. From there the method 400 proceeds to the exit Terminal F and finishes execution.

While the preferred embodiment of the invention has been illustrated and described, it will be appreciated that various changes can be made therein without departing from the spirit and scope of the invention.

The invention claimed is:

1. A method for ordering drug samples comprising the steps of:
   providing a drug sample fulfillment platform that is Web based and responds to an access request of a user including a prescriber and a sales representative;
   receiving said access request via the Internet from a brand Web site or another brand Web site;
   providing a set of brand rules which include physical samples, vouchers, or coupons for guiding a distributor of drug samples of a drug to cause one prescriber's drug sample availability and characteristics, such as the time frame, dosages and quantity while a member of said brand Web site to be different from those of the same prescriber while a member of said another brand Web site; and
   creating a transaction that includes said sales representative accessing said drug sample fulfillment platform for said prescriber with an identifier of said sales representative in order to open the drug sample fulfillment platform within said brand website or said another brand website and order drug samples for said prescriber, the drug sample fulfillment platform electronically notifying the sales representative about the availability of drug samples.

2. The method of claim 1, further comprising receiving medical practice specialty of the prescriber, wherein the set of brand rules defines the availability of drug samples available to the prescriber depending on his medical practice specialty.

3. The method of claim 1, further comprising receiving a unique global identifier that identifies the prescriber who prescribes drugs in the United States, wherein the set of brand rules defines the availability of drug samples available to the prescriber depending on his unique global identifier.

4. The method of claim 1, further generating a personalized list of drug samples that are available to the prescriber to obtain.

5. The method of claim 4, further comprising displaying a drug sample by its name, strength, and quantity, and receiving via the Internet a selection of drug samples.

6. The method of claim 5, further comprising receiving a delivery address, phone, fax, and medical state license number to enable fulfillment of the selected drug sample.

7. The method of claim 6, further comprising recording the selection activities of the drug sample in a request database.

8. A system for ordering drug samples comprising:
   hardware configured to run software for a dru9 sample fulfillment platform, that responds to an access request of a user including a prescriber or a sales representative, said drug sample fulfillment platform includes a pharma rules sample engine configured to modify allocation of drug samples to a prescriber based on its monitoring of drug samples provided to the prescriber;
   said access request to said drug sample fulfillment platform is received via the Internet from a brand Web site or another brand Web site;
   a set of brand rules which include physical samples, vouchers or coupons, for guiding a distributor of drug samples of a drug to cause one prescriber's drug sample availability and characteristics, such as the time frame, dosages and quantity, while a member of said brand Web site to be different from those of the same prescriber while a member of said other brand Web site; and
   said sales representative accesses said drug samples fulfillment platform with an identifier in order to open said drug sample fulfillment platform within said brand Web site or said another brand Web site and order drug samples for said prescriber, said sample fulfillment platform electronically notifying the sales representative about the availability of drug samples.

9. The system of claim 8, further comprising hardware configured to run software for receiving medical practice specialty of the prescriber, wherein the set of brand rules defines the availability of drug samples available to the prescriber depending on his medical practice specialty.

10. The system of claim 8, further comprising hardware configured to run software for receiving a unique global identified that identifies the prescriber who prescribes drugs in the United States, wherein the set of brand rules defines the availability of drug samples available to the prescriber depending on his unique global identifier.

11. The system of claim 8, further comprising hardware configured to run software for generating a personalized list of drug samples that are available to the prescriber to obtain.

12. The system of claim 11, further comprising comprising hardware configured to run software for displaying a drug sample by its name, strength, and quantity, and receiving via the Internet a selection of the drug sample.

13. The system of claim 12, further comprising comprising hardware configured to run software for receiving a delivery address, phone, fax, and medial state license number to enable fulfillment of the selected drug sample.

14. The system of claim 13, further comprising comprising hardware configured to run software for recording the selection activities of the drug sample in a request database.

15. A non-transitory computer-readable medium comprising stored computer- executable instructions to implement a method for ordering drug samples, comprising the steps of:
   providing a drug sample fulfillment platform that responds to an access request of a user including a prescriber and a sales representative;
   receiving said access request via the Internet from a pharma brand Web site or another pharma brand Web site;
   providing a set of brand rules which include physical samples, vouchers, or coupons for guiding a distributor of drug samples of a drug to cause one prescriber's drug sample availability and characteristics, such as the time frame, dosages and quantity while a member of said pharma brand Web site to be different from those of the same prescriber while a member of said another pharma brand Web site; and
   creating a transaction that includes said sales representative accessing said drug sample fulfillment platform with an identifier of said sales representative in order to open the drug sample fulfillment platform within said pharma brand website or said another pharma brand website and drug samples for said prescriber, the drug sample fulfillment platform electronically notifying the sales representative about the availability of drug samples.

16. The non-transitory computer-readable medium of claim 15, further comprising receiving medical practice specialty of the prescriber, wherein the set of brand rules defines the availability of drug samples available to the prescriber depending on his medical practice specialty.

17. The non-transitory computer-readable medium of claim 15, further comprising receiving a unique global identifier that identifies the prescriber who prescribes drugs in the United States, wherein the set of brand rules defines the availability of drug samples available to the prescriber depending on his unique global identifier.

18. The non-transitory computer-readable medium of claim 15, further generating a personalized list of drug samples that are available to the prescriber to obtain.

19. The non-transitory computer-readable medium of claim 18, further comprising displaying a drug sample by its name, strength, and quantity, and receiving via the Internet a selection of drug samples.

20. The non-transitory computer-readable medium of claim 19, further comprising receiving a delivery address, phone, fax, and medial state license number to enable fulfillment of the selected drug sample.

* * * * *